United States Patent
Lavigne et al.

(10) Patent No.: US 8,927,293 B2
(45) Date of Patent: Jan. 6, 2015

(54) METHODS AND DEVICES FOR ANALYTICAL SENSING OF BIOGENIC AMINES

(75) Inventors: John J. Lavigne, Columbia, SC (US); Toby Nelson, Pittsburgh, PA (US); Marc Maynor, Columbia, SC (US)

(73) Assignee: University of South Carolina, Columbia, SC (US)

(*) Notice: Subject to any disclaimer, the term of this patent is extended or adjusted under 35 U.S.C. 154(b) by 1158 days.

(21) Appl. No.: 12/079,105

(22) Filed: Mar. 24, 2008

(65) Prior Publication Data

US 2008/0299669 A1 Dec. 4, 2008

Related U.S. Application Data

(60) Provisional application No. 60/919,763, filed on Mar. 23, 2007.

(51) Int. Cl.
- *G01N 33/00* (2006.01)
- *G01N 21/77* (2006.01)
- *G01N 33/52* (2006.01)
- *G01N 21/78* (2006.01)

(52) U.S. Cl.
CPC .............. *G01N 21/77* (2013.01); *G01N 33/523* (2013.01); *G01N 21/78* (2013.01); *G01N 2021/7759* (2013.01); *G01N 2021/7766* (2013.01)
USPC .............................. 436/111; 436/73; 436/106

(58) Field of Classification Search
CPC .......... G01N 31/22; G01N 2021/7786; G01N 2291/0255; G01N 21/78; G01N 21/77; G01N 33/52; G01N 33/523
See application file for complete search history.

(56) References Cited

U.S. PATENT DOCUMENTS

2005/0191704 A1  9/2005  Boga et al.

OTHER PUBLICATIONS

Davis et al. "High-Performance Liquid—Chromatographic Separation and Fluorescence Measurement of Biogenic Amines in Plasma, Urine, and Tissue." 1978. Clin. Chem. vol. 24, No. 8, pp. 1317-1324.*
Nelson et al. "Cross-Reactive Conjugated Polymers: Analyte-Specific Aggregative Response for Structurally Similar Diamines". 2006. J. Am. Chem. Soc. vol. 128, pp. 5640-5641.*
Qin et al., "Optical Sensor for Amine Vapors Based on Dimer-Monomer Equilibrium of Indium(III) Octaethylporphyrin in a Polymeric Film", Anal. Chem., 2003, 75, 332-340.*
Lodeira and Pina, "Luminescent and chromogenic molecular probes based on polyamines and related compounds" Coordination Chemistry Reviews, 2009, v. 253, pp. 1353-1383.*
Williams, "The Symbiosis of Metal ion and Protein Chemistry", Pure & Appl. Chem., 1983, vol. 55, No. 1, pp. 35-46.*
"Effect of metal Ions (Ni2+, Cu2+ and Zn2+) and water coordination on the structure of L-phenylalanine, L-tyrosine, L-tryptophan and their zwitterionic forms", J. Mol. Model, 2011, v. 17, pp. 3117-3128.*
Jeffries-El et al., "In Situ End Group Modification of Regioregular Poly(3-Alkylthiophene) Using the Grignard Metathesis Polymerization Method," *Advanced Materials*, 16(12):1017-1019 (2004).

(Continued)

*Primary Examiner* — Yelena G Gakh
(74) *Attorney, Agent, or Firm* — Ballard Spahr LLP

(57) ABSTRACT

Disclosed herein are chromogenic response polymers and methods and devices that utilize the disclosed polymers which are suitable for use in detecting the presence of and identity of biogenic amines.

20 Claims, 16 Drawing Sheets
(2 of 16 Drawing Sheet(s) Filed in Color)

(56) References Cited

OTHER PUBLICATIONS

Liu et al., "End Group Modification of Regioregular Polythiophene through Postpolymerization Functionalization," *Macromolecules*, 35:9882-9889 (2002).

McCullough et al., "Self-Assembly and Disassembly of Regioregular, Water Soluble Polythiophenes: Chemoselective Ionchromatic Sensing in Water," *J. Am. Chem. Soc.*, 119:633-634 (1997).

Sheina et al., "Chain Growth Mechanism for Regioregular Nickel-Initiated Cross-Coupling Polymerizations," *Macromolecules*, 37:3526-3528 (2004).

Stokes et al., "New Phosphonic Acid Functionalized, Regioregular Polythiophenes," *Macromolecules*, 36:7114-7118 (2003).

Zhai et a., "A Simple Method to Generate Side-Chain Derivatives of Regioregular Polythiophene via the GRIM Metathesis andPost-Polymerization Functionalization," *Macromolecules*, 36:61-64 (2003).

Ewbank et al., "Regioregular poly(thiophene-3-alkanoic acid)s: water soluble conducting polymers suitable for chromatic chemosensing in solution and solid state," *Tetrahedron*, 60:11269-11275 (2004).

\* cited by examiner

METHODS AND DEVICES FOR ANALYTICAL SENSING OF BIOGENIC AMINES

This application claims priority to the U.S. Provisional Application No. 60/919,763, filed Mar. 23, 2007, the disclosure of which application is hereby incorporated in its entirety by this reference.

FIELD

Disclosed herein are chromogenic responsive polymers and methods and devices that utilize the disclosed polymers which are suitable for use in detecting the presence of and identity of biogenic amines.

BACKGROUND

The ability to sense or measure a physical quantity or chemical substance has been a desirable research endeavor for decades. Increasingly, there exists a need for rapid, accurate, reproducible, and economical sensors. Of particular interest to many are sensors capable of detecting biologically relevant analytes. A method for the accurate detection, quantification, and discrimination of biological molecules would be of great benefit to many technical fields including biochemistry, food science, and medicine.

Technology capable of sensing biologically relevant analytes exists. Noteworthy are electronic nose and tongue technologies that are finding increasing utility in the food science industry. While these technologies and technologies alike are able to identify different classes of analytes, their ability to discriminate between analytes of the same class is limited. One class of analytes that can often be difficult to detect and discriminate between as well as from among other analytes is biogenic amines. Biogenic amines have been associated with a variety of problems in the food science and medical industries. An increased production of biogenic amine by an organism, for example, can result from rapid cell proliferation. Consequently, biogenic amine levels can serve as indicators of health complications, including cancer, bacterial infection, and food poisoning, to name a few. If a human, for example, is exposed to elevated biogenic amine levels present in food, this exposure can trigger a wide range of symptoms ranging from headaches to life-threatening episodes of blood pressure spikes.

Biogenic amines can also serve as indicators of food spoilage caused by bacteria (i.e. to indirectly detect the presence of bacteria). Food spoilage (e.g., meat and fish spoilage) occurs as bacteria begin to grow shortly after the time of slaughter. During the initial stages of food spoilage, free amino acids are decarboxylated by enzymes released by invading spoilage microorganisms. The product of decarboxylation includes biogenic amines, namely putrescine and cadaverine. These two amines are particularly distinctive in odor and correlate well with surface bacterial counts. Another product, histamine, is of interest due to its alleged ability to induce histamine intoxication, a form of food poisoning associated with the consumption of spoiled fish.

Several methods exist for detecting biogenic amines. Classical methods for detecting biogenic amines include chromatographic techniques, such as gas chromatography, thin layer chromatography, reversed phase liquid chromatography, and liquid chromatography. However, these techniques often require sample pre-treatment and relatively long analysis time, which can increase costs and thereby make many of these methods not suitable for routine use. Other more advanced methods for detecting biogenic amines include the use of molecular imprinted polymers (MIPs), enzymes, antibodies, single molecule, and array based sensors.

Although current amine sensors (e.g., biogenic amine sensors) show promise, there is still a need to identify and develop new and improved sensors. Particularly, a need exists for technology capable of discriminating analytes within the same or similar class of analytes.

SUMMARY

In accordance with the purposes of the disclosed materials, compositions, articles, devices, and methods, as embodied and broadly described herein, the disclosed subject matter, in one aspect, relates to compounds and compositions (e.g., poly(thiophene) and poly(thiophene) derivatives) and methods for providing and using such compounds and compositions. In another aspect, the disclosed subject matter relates to devices comprising the disclosed compounds and compositions.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying figures, which are incorporated in and constitute a part of this specification, illustrate several aspects described below.

The application file contains at least one photograph executed in color. Copies of this patent application publication with color photographs will be providing by the Office upon request and payment of the necessary fee.

DETAILED DESCRIPTION

Figure 1:
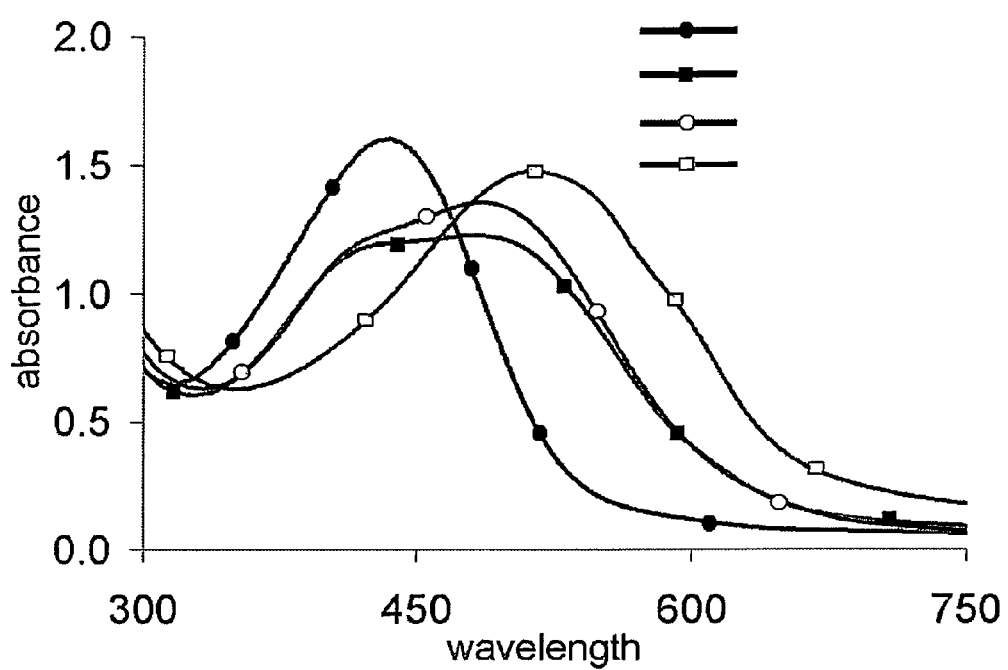
FIG. 1 depicts the absorbance spectrum of a series of solution comprising the chromogenic polymer of Example 1. The curve indicated with a solid circle is the absorbance spectrum obtained of the polymer alone (control), the curve indicated with a solid square is the absorbance spectrum obtained from a solution of the polymer in the presence of 1,2-ethylenediamine, the curve indicated with a clear circle is the absorbance spectrum obtained from a solution of the polymer in the presence of 1,4-butylenediamine, and the curve indicated with a clear square is the absorbance spectrum obtained from a solution of the polymer in the presence of 1,6-hexylenediamine.
Figure 2:
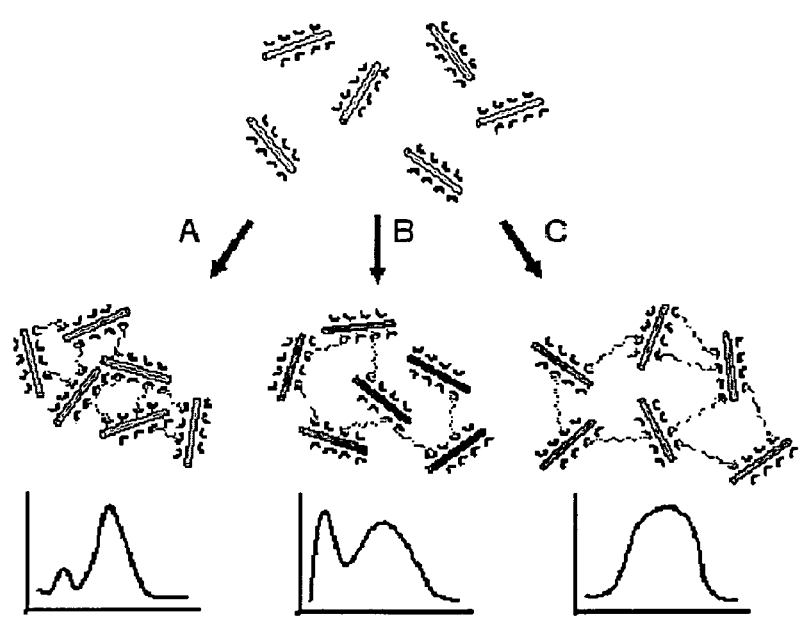
FIG. 2 depicts a representation of the aggregative interactions between a disclosed poly(thiophene) and three diamines having differing lengths.

The materials, compounds, compositions, articles, and methods described herein may be understood more readily by reference to the following detailed description of specific aspects of the disclosed subject matter and the Examples included therein and to the Figures.

Before the present materials, compounds, compositions, articles, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

In this specification and in the claims that follow, reference will be made to a number of terms, which shall be defined to have the following meanings:

Throughout this specification, unless the context requires otherwise, the word "comprise," or variations such as "comprises" or "comprising," will be understood to imply the inclusion of a stated integer or step or group of integers or steps but not the exclusion of any other integer or step or group of integers or steps.

It must be noted that, as used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

A weight percent of a component, unless specifically stated to the contrary, is based on the total weight of the formulation or composition in which the component is included.

By "contacting" is meant the physical contact of at least one substance to another substance.

By "sufficient amount" and "sufficient time" means an amount and time needed to achieve the desired result or results, e.g., dissolve a portion of the polymer.

"Admixture" or "blend" as generally used herein means a physical combination of two or more different components. In the case of polymers, an admixture, or blend, of polymers is a physical blend or combination of two or more different polymers as opposed to a copolymer which is single polymeric material that is comprised of two or more different monomers.

"Absorbable" as used herein means the complete degradation of a material in vivo, and elimination of its metabolites from an animal or human subject.

"Molecular weight" as used herein, unless otherwise specified, refers generally to the relative average molecular weight of the bulk polymer. In practice, molecular weight can be estimated or characterized in various ways including gel permeation chromatography (GPC) or capillary viscometry. GPC molecular weights are reported as the weight-average molecular weight (Mw) or as the number-average molecular weight (Mn). Capillary viscometry provides estimates of molecular weight as the Inherent Viscosity (IV) determined from a dilute polymer solution using a particular set of concentration, temperature, and solvent conditions. Unless otherwise specified, IV measurements are made at 30° C. on solutions prepared in chloroform at a polymer concentration of 0.5 g/dL.

"Analyte" as used herein, unless otherwise specified, refers to a sample solution that contains one or more amines. The analyte can be a sample directly taken from a source to be tested or the analyte can be a solution, for example, a buffered solution into which a sample has been placed prior to contacting the analyte with the disclosed polymers or prior to being analyzed by the methods, devices, and/or kits disclosed herein.

Substituted and unsubstituted acyclic units comprising from 1 to 24 carbon atoms encompass 3 categories of units: linear or branched alkyl, non-limiting examples of which include, methyl ($C_1$), ethyl ($C_2$), n-propyl ($C_3$), iso-propyl ($C_3$), n-butyl ($C_4$), sec-butyl ($C_4$), iso-butyl ($C_4$), tert-butyl ($C_4$), and the like; substituted linear or branched alkyl, non-limiting examples of which includes, hydroxymethyl ($C_1$), chloromethyl ($C_1$), trifluoromethyl ($C_1$), aminomethyl ($C_1$), 1-chloroethyl ($C_2$), 2-hydroxyethyl ($C_2$), 1,2-difluoroethyl ($C_2$), 3-carboxypropyl ($C_3$), and the like; linear or branched alkenyl, non-limiting examples of which include, ethenyl ($C_2$), 3-propenyl ($C_3$), 1-propenyl (also 2-methylethenyl) ($C_3$), isopropenyl (also 2-methylethen-2-vi) ($C_3$), buten-4-yl ($C_4$), and the like; substituted linear or branched alkenyl, non-limiting examples of which include, 2-chloroethynyl (also 2-chlorovinyl) ($C_2$), 4-hydroxybutan-1-yl ($C_4$), 7-hydroxy-7-methyloct-4-en-2-yl ($C_9$), 7-hydroxy-7-methyloct-3,5-dien-2-yl ($C_9$), and the like; and linear or branched alkynyl, non-limiting examples of which include, ethynyl ($C_2$), prop-2-ynyl (also propargyl) ($C_3$), propyn-1-yl ($C_3$), and 2-methyl-hex-4-yn-1-yl ($C_7$); substituted linear or branched alkynyl, non-limiting examples of which include, 5-hydroxy-5-methylhex-3-ynyl ($C_7$), 6-hydroxy-6-methylhept-3-yn-2-yl ($C_8$), 5-hydroxy-5-ethylhept-3-ynyl ($C_9$), and the like.

Substituted and unsubstituted cyclic units comprising from 3 to 24 carbon atoms encompass the following units: carbocyclic rings having a single substituted or unsubstituted hydrocarbon ring, non-limiting examples of which include, cyclopropyl ($C_3$), 2-methyl-cyclopropyl ($C_3$), cyclopropenyl ($C_3$), cyclobutyl ($C_4$), 2,3-dihydroxycyclobutyl ($C_4$), cyclobutenyl ($C_4$), cyclopentyl ($C_5$), cyclopentenyl ($C_5$), cyclopentadienyl ($C_5$), cyclohexyl ($C_6$), cyclohexenyl ($C_6$), cycloheptyl ($C_7$), cyclooctanyl ($C_8$), decalinyl ($C_{10}$), 2,5-dimethylcyclopentyl ($C_5$), 3,5-dichlorocyclohexyl ($C_6$), 4-hydroxycyclohexyl ($C_6$), and 3,3,5-trimethylcyclohex-1-yl ($C_6$); carbocyclic rings having two or more substituted or unsubstituted fused hydrocarbon rings, non-limiting examples of which include, octahydropentalenyl ($C_8$), octahydro-1H-indenyl ($C_9$), 3a,4,5,6,7,7a-hexahydro-3H-inden-4-yl ($C_9$), decahydroazulenyl ($C_{10}$); and carbocyclic rings which are substituted or unsubstituted bicyclic hydrocarbon rings, non-limiting examples of which include, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

Substituted and unsubstituted aryl units comprising from 6 to 24 carbon atoms encompass the following units: $C_6$, $C_{10}$, or $C_{14}$ substituted or unsubstituted aryl rings; phenyl, naphthyl, anthracenyl, phenanthryl, and the like whether substituted or unsubstituted, non-limiting examples of which include, phenyl ($C_6$), naphthylene-1-yl ($C_{10}$), naphthylene-2-yl ($C_{10}$), 4-fluorophenyl ($C_6$), 2-hydroxyphenyl ($C_6$), 3-methylphenyl ($C_6$), 2-amino-4-fluorophenyl ($C_6$), 2-(N,N-diethylamino) phenyl ($C_6$), 2-cyanophenyl ($C_6$), 2,6-di-tert-butylphenyl ($C_6$), 3-methoxyphenyl ($C_6$), 8-hydroxynaphthylen-2-yl ($C_{10}$), 4,5-dimethoxynaphthylen-1-yl ($C_{10}$), and 6-cyano-naphthylene-1-yl ($C_{10}$); $C_6$, $C_{10}$, or $C_{14}$ aryl rings fused with 1 or 2 saturated rings non-limiting examples of which include, bicyclo[4.2.0]octa-1,3,5-trienyl ($C_8$), and indanyl ($C_9$).

Substituted and unsubstituted heterocyclic or heteroaryl units comprising from 1 to 24 carbon atoms encompasses the following units all of which contain at least one heteroatom in at least one ring chosen from nitrogen (N), oxygen (O), sulfur (S), phosphorous (P) or mixtures of N, O, S, and P: heterocyclic units having a single ring containing one or more heteroatoms chosen from nitrogen (N), oxygen (O), or sulfur (S), or mixtures of N, O, and S, non-limiting examples of which include, diazirinyl ($C_1$), aziridinyl ($C_2$), urazolyl ($C_2$), azetidinyl ($C_3$), pyrazolidinyl ($C_3$), imidazolidinyl ($C_3$), oxazolidinyl ($C_3$), isoxazolinyl ($C_3$), isoxazolyl ($C_3$), thiazolidinyl ($C_3$), isothiazolyl ($C_3$), isothiazolinyl ($C_3$), oxathiazolidinonyl ($C_3$), oxazolidinonyl ($C_3$), hydantoinyl ($C_3$), tetrahydrofuranyl ($C_4$), pyrrolidinyl ($C_4$), morpholinyl ($C_4$), piperazinyl ($C_4$), piperidinyl ($C_4$), dihydropyranyl ($C_5$), tetrahydropyranyl ($C_5$), piperidin-2-onyl (valerolactam) ($C_5$), 2,3,4,5-tetrahydro-1H-azepinyl ($C_6$), 2,3-dihydro-1H-indole ($C_8$), and 1,2,3,4-tetrahydro-quinoline ($C_9$); heterocyclic units having 2 or more rings one of which is a heterocyclic ring, non-limiting examples of which include hexahydro-1H-pyrrolizinyl ($C_7$), 3a,4,5,6,7,7a-hexahydro-1H-benzo[d]imidazolyl ($C_7$), 3a,4,5,6,7,7a-hexahydro-1H-indolyl ($C_8$), 1,2,3,4-tetrahydroquinolinyl ($C_9$), and decahydro-1H-cycloocta[b]pyrrolyl ($C_{10}$); heteroaryl rings containing a single ring, non-limiting examples of which include, 1,2,3,4-tetrazolyl ($C_1$), [1,2,3]triazolyl ($C_2$), [1,2,4]triazolyl ($C_2$), triazinyl ($C_3$), thiazolyl ($C_3$), 1H-imidazolyl ($C_3$), oxazolyl ($C_3$), furanyl ($C_4$), thiopheneyl ($C_4$), pyrimidinyl ($C_4$), 2-phenylpyrimidinyl ($C_4$), pyridinyl ($C_5$), 3-methylpyridinyl ($C_5$), and 4-dimethylaminopyridinyl ($C_5$); heteroaryl rings containing 2 or more fused rings one of which is a heteroaryl ring, non-limiting examples of which include: 7H-purinyl ($C_5$), 9H-purinyl ($C_5$), 6-amino-9H-purinyl ($C_5$), 5H-pyrrolo[3,2-d]pyrimidinyl ($C_6$), 7H-pyrrolo[2,3-d]pyrimidinyl ($C_6$), pyrido[2,3-d]pyrimidinyl ($C_7$), 2-phenylbenzo[d]thiazolyl ($C_7$), 1H-indolyl ($C_8$), 4,5,6,7-tetrahydro-1-H-indolyl ($C_8$), quinoxalinyl ($C_8$), 5-methylquinoxalinyl ($C_8$), quinazolinyl ($C_8$), quinolinyl ($C_9$), 8-hydroxy-quinolinyl ($C_9$), and isoquinolinyl ($C_9$).

The term "arylalkylene" is used throughout the specification to refer to substituted or unsubstituted $C_6$, $C_{10}$, or $C_{14}$ aryl rings tethered to another unit through a substituted or unsubstituted $C_1$-$C_{12}$ alkylene unit. These units can be referred to by indicating the number of carbons contained in the alkylene unit followed by the number of carbon atoms in the aryl unit, or by their chemical name. A non-limiting example of tethered cyclic hydrocarbyl units includes a substituted or unsubstituted benzyl. A substituted or unsubstituted benzyl unit contains a tether containing one carbon atom (methylene) and a substituted or unsubstituted aryl ring containing six carbon atoms, or a $C_1$-($C_6$) unit, having the formula:

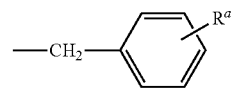

wherein $R^a$ is optionally one or more independently chosen substitutions for hydrogen. Further examples include other aryl units, inter alia, (2-hydroxyphenyl)hexyl $C_6$-($C_6$); naphthalen-2-ylmethyl $C_1$-($C_{10}$), 4-fluorobenzyl $C_1$-($C_6$), 2-(3-hydroxy-phenyl)ethyl $C_2$-($C_6$), as well as substituted and unsubstituted $C_3$-$C_{10}$ alkylenecarbocyclic units, for example, cyclopropylmethyl $C_1$-$(C_3)$, cyclopentylethyl $C_2$-$(C_5)$, cyclohexylmethyl $C_1$-$(C_6)$.

The terms "heteroarylalkylene" and "heterocyclicalkylene" are used throughout the specification to refer to substituted or unsubstituted heteroaryl and heterocyclic rings as defined herein above containing from 1 to 24 carbon atoms that are tethered to another unit through a substituted or unsubstituted $C_1$-$C_{12}$ alkylene unit. These units can be referred to by indicating the number of carbons contained in the alkylene unit followed by the number of carbon atoms in the heteroaryl and heterocyclic unit, or by their chemical name. A non-limiting example includes substituted and unsubstituted $C_1$-$C_{10}$ alkylene-heteroaryl units, for example a 2-picolyl $C_1$-$(C_6)$ unit having the formula:

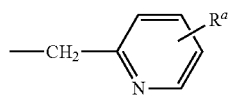

wherein $R^a$ is the same as defined above. In addition, $C_1$-$C_{12}$ tethered cyclic hydrocarbyl units include $C_1$-$C_{10}$ alkyleneheterocyclic units and alkylene-heteroaryl units, non-limiting examples of which include, aziridinylmethyl $C_1$-$(C_2)$ and oxazol-2-ylmethyl $C_1$-$(C_3)$.

Reference will now be made in detail to specific aspects of the disclosed materials, compounds, compositions, articles, and methods, examples of which are illustrated in the accompanying Examples.

Disclosed herein are materials, compounds, compositions, and components that can be used for, can be used in conjunction with, can be used in preparation for, or are products of the disclosed methods, devices, and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a composition is disclosed and a number of modifications that can be made to a number of components or residues of the composition are discussed, each and every combination and permutation that are possible are specifically contemplated unless specifically indicated to the contrary. Thus, if a class of polymers A, B, and C are disclosed as well as a class of polymers D, E, and F, and an example of a copolymer A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific aspect or combination of aspects of the disclosed methods, and that each such combination is specifically contemplated and should be considered disclosed.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

The disclosed methods and articles comprise one or more chromogenic polymers. Without wishing to be limited by theory, amines or polyamines interact with the chromogenic polymers in solution to cause a distinct color change that can be equated to the presence of a particular amine. Of particular importance are diamines and polyamines, inter alia, the degradation products of amino acids; putrescine, cadaverine, histamine, spemine and spermidine. The diamines interact with the chromogenic polymers to affect one or more bulk properties and or molecular level events of the polymer, for example, the length of polymer conjugation, change in polymer aggregation, and therefore changing the absorption spectrum of a solution of the disclosed chromogenic polymers. The change in bulk properties also results in the scattering of visible light by the solutions containing an amine.

Of particular interest in the food industry and to the consumer is the ability to detect the presence of amines that can signal either spoilage of beef, fish, chicken, pork, and the like, but whether spoilage has begun and to what degree spoilage, if any, has occurred. In addition, the disclosed methods can be used to identify the presence of biologically important amines. Non-limiting examples of amines include 1,2-ethylenediamine, putrescine, cadaverine, agmatine, spermine, spermidine, tryptamine, histamine, phenylethylamine, tyramine, serotonin, and dopamine.

One aspect of the disclosed methods and articles relates to identifying the presence of one or more amines chosen from:

i) ethylenediamine:

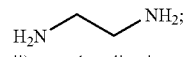

ii) propylenediamine:

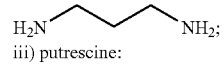

iii) putrescine:

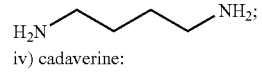

iv) cadaverine:

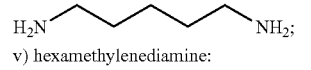

v) hexamethylenediamine:

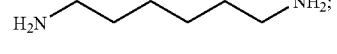

vi) spemidine:

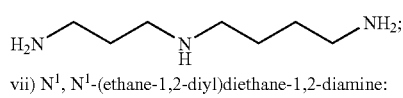

vii) N¹, N¹-(ethane-1,2-diyl)diethane-1,2-diamine:

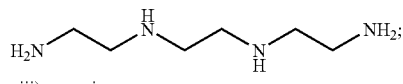

viii) spermine:

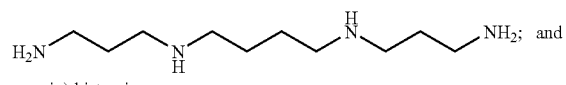

ix) histamine:

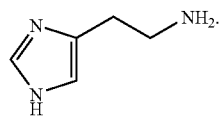

CHROMOGENIC POLYMERS

The disclosed methods and articles utilize chromogenic polymers. The chromogenic polymers as further described herein are polymers comprising a conjugated backbone. Conjugated polymers have been used as chemical and biological sensors because, at least in part, of their distinctive optical and electronic properties. For example, conjugated polymers have been used for the detection of inorganic ions, small organic compounds, DNA, proteins, and for the determination of stereochemistry. A principal signal transduction mechanism for these materials has relied on the planarization/deplanarization (i.e., a single structural change) of the polymer backbone upon exposure of the side-chain functional group to an analyte. As a result, methods relying on a signal transduction mechanism (i.e. a single perturbation) can be limited to a single-dimensional response that is often expressed as a function of the change of one or two wavelengths (if the signal is optical, for example) in a relevant polymer spectrum.

Disclosed herein is an alternative approach based on a multistate, multidimensional response derived from numerous dynamic polymer-analyte interactions. While not wishing to be bound by theory, it is believed that such dynamic polymer-analyte interactions cause main-chain conformational changes, as well as π-π stacking between polymer chains and scattering of visible light caused by the solution stable polymer-analyte aggregates. It should be appreciated that given such a dynamic equilibrium between a polymer and an analyte exists, multiple assemblies can, at least in theory, form in solution, each of which can have their own distinctive spectral properties. Thus, disclosed herein are methods aimed at harnessing a collective response from multiple interactions that characterize the overall shape of a spectrum, thereby enabling the discrimination between specific compounds that are found in the analytes or the concentration of a compound or compounds in the analyte solution.

The disclosed chromogenic polymers comprise a backbone having a plurality of one or more conjugated ring systems and a substrate recognition element. Non-limiting examples of backbone elements include thiophenyl, furanyl, pyrrolyl, fluorenyl, 1,4-phenylene ethynylene, and 1,4-phenylene. Non-limiting examples of chromogenic polymer backbones include:

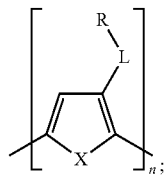  i)

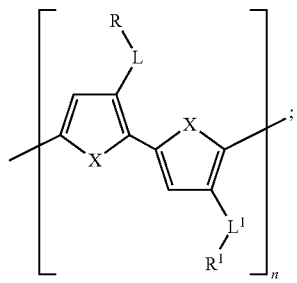  ii)

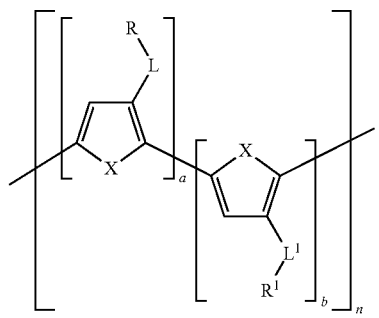  iii)

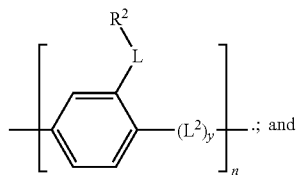  iv)

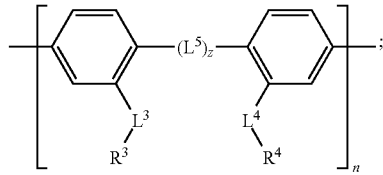  v)

wherein the index n has a value such that the polymer has a molecular weight of from about 1,000 Da to about 2,000,000 Da. The disclosed chromogenic response polymers have an average molecular weight of from about 1000 Da to about 2,000,000 Da. In one embodiment, the disclosed chromogenic response polymers have an average molecular weight of from about 1000 Da to about 1,000,000 Da. In another embodiment, the disclosed chromogenic response polymers have an average molecular weight of from about 1000 Da to about 20,000 Da. In a further embodiment, the disclosed chromogenic response polymers have an average molecular weight of from about 1000 Da to about 10,000 Da. In a yet another embodiment, the disclosed chromogenic response polymers have an average molecular weight of from about 5,000 Da to about 10,000 Da. In a still further embodiment, the disclosed chromogenic response polymers have an average molecular weight of from about 3,000 Da to about 8,000 Da. In a yet further embodiment, the disclosed chromogenic response polymers have an average molecular weight of from about 5,000 Da to about 20,000 Da. In a still yet further embodiment, the disclosed chromogenic response polymers have an average molecular weight of from about 10,000 Da to about 20,000 Da. In one further embodiment, the disclosed chromogenic response polymers have an average molecular weight of from about 2,000 Da to about 5,000 Da. However, the disclosed polymers can have any average molecular weight, for example, 1,000 Da, 1,500 Da, 2,000 Da, 2,500 Da, 3,000 Da, 3,500 Da, 4,000 Da, 4,500 Da, 5,000 Da, 5,500 Da, 6,000 Da, 6,500 Da, 7,000 Da, 7,500 Da, 8,000 Da, 8,500 Da, 9,000 Da, 9,500 Da, or 10,000 Da rounded to the nearest 500 Da. However, the polymers can have any discrete average molecular weight, for example, 8,020 Da, 8,033 Da, 8,115 Da, 9,456 Da, and the like. Therefore, the ranges of the various embodiments include all values of average molecular weight within the range.

The average molecular weights of the disclosed polymers are determined using only the backbone units prior to addition of the substrate recognition elements, inter alia, transition metals. The backbone unit having the formula:

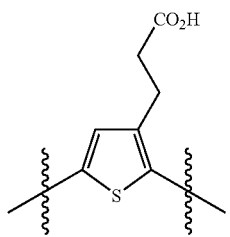 [SMILES: *c1cc(CCC(=O)O)c(*)s1]

has an approximate molecular weight of 154 g/mol, therefore, a chromogenic polymer having an average molecular weight of approximately 1,500 Da will comprise about 10 of these units in the backbone of the chromogenic polymer.

X Units

X can be S, N, or O. When X is a sulfur atom, the chromogenic polymers are poly(thiophene)s. When X is a nitrogen atom, the chromogenic polymers are poly(pyrrole)s. When X is an oxygen atom, the chromogenic polymers are poly(furan)s. However, the disclosed polymers can have an admixture of different units, for example, a mixture of thiophene units and furan units.

R Units

R units are moieties that interact with the disclosed biogenic amines. R units are independently chosen from one another. R units serve as a moiety that complexes with the one or more substrate recognition elements and therefore serve to differentiate between different biogenic amines. Non-limiting examples of R units include:

i) —H;
ii) —OM;
iii) —CO$_2$M;
iv) —SO$_3$M;
v) —PO$_3$M$_2$; and
vi) —OCH$_3$;

wherein M is hydrogen, ammonium, alkyl ammonium, an alkali metal, an alkali earth metal, a transition metal, a lanthanide metal, or mixtures thereof.

In one aspect of the disclosed chromogenic polymers, R units comprise a carboxylate unit. Non-limiting examples of this aspect of R units include:

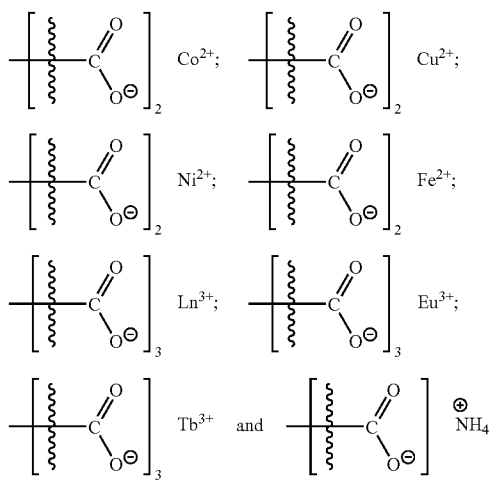

In another aspect of the disclosed chromogenic polymers, R units comprise a sulfonate unit. Non-limiting examples of this aspect of R units include:

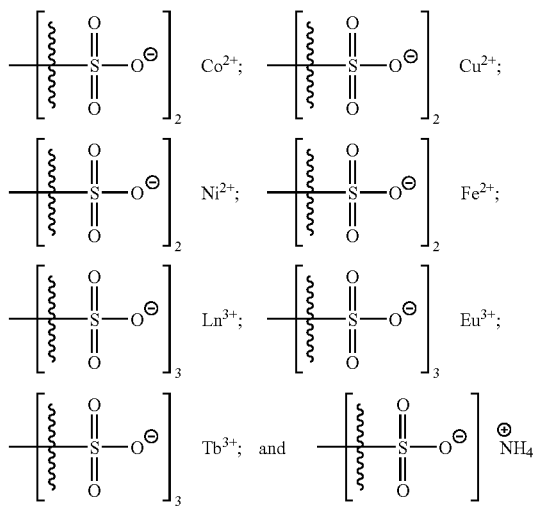

In a further aspect of the disclosed chromogenic polymers, R units comprise a phosphonate unit. Non-limiting examples of this aspect of R units include:

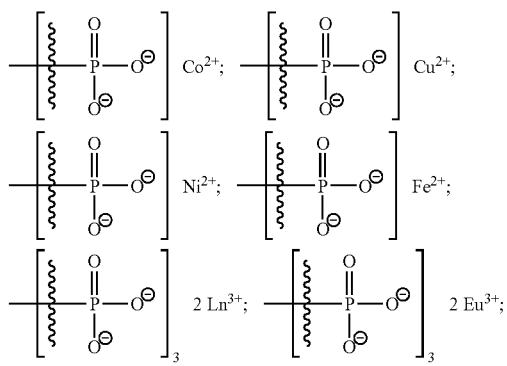

-continued

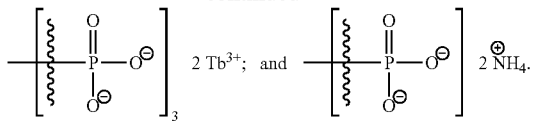

In a yet further aspect of the disclosed chromogenic polymers, R units are an admixture of charged units and non-charged units. In one embodiment of this aspect, the chromogenic polymers comprise a mixture of R units wherein at least 90% of the R units are carboxylate units and 10% of the R units are hydrogen. In another embodiment of this aspect, the chromogenic polymers comprise a mixture of R units wherein at least 80% of the R units are carboxylate units and 20% of the R units are hydrogen. In a further embodiment of this aspect, the chromogenic polymers comprise a mixture of R units wherein at least 70% of the R units are carboxylate units and 30% of the R units are hydrogen. In a yet further embodiment of this aspect, the chromogenic polymers comprise a mixture of R units wherein at least 60% of the R units are carboxylate units and 40% of the R units are hydrogen. In a still further embodiment of this aspect, the chromogenic polymers comprise a mixture of R units wherein at least 50% of the R units are carboxylate units and 50% of the R units are hydrogen. However, I one aspect of the disclosed polymers, all of the R units are protonated.

In a further embodiment of this aspect, the chromogenic polymers comprise a mixture of R units wherein at least 90% of the R units are sulfonate units and 10% of the R units are hydrogen. In another embodiment of this aspect, the chromogenic polymers comprise a mixture of R units wherein at least 80% of the R units are sulfonate units and 20% of the R units are hydrogen. In a further embodiment of this aspect, the chromogenic polymers comprise a mixture of R units wherein at least 70% of the R units are sulfonate units and 30% of the R units are hydrogen. In a yet further embodiment of this aspect, the chromogenic polymers comprise a mixture of R units wherein at least 60% of the R units are sulfonate units and 40% of the R units are hydrogen. In a still further embodiment of this aspect, the chromogenic polymers comprise a mixture of R units wherein at least 50% of the R units are sulfonate units and 50% of the R units are hydrogen.

In a yet further embodiment of this aspect, the chromogenic polymers comprise a mixture of R units wherein at least 90% of the R units are phosphonate units and 10% of the R units are hydrogen. In another embodiment of this aspect, the chromogenic polymers comprise a mixture of R units wherein at least 80% of the R units are phosphonate units and 20% of the R units are hydrogen. In a further embodiment of this aspect, the chromogenic polymers comprise a mixture of R units wherein at least 70% of the R units are phosphonate units and 30% of the R units are hydrogen. In a yet further embodiment of this aspect, the chromogenic polymers comprise a mixture of R units wherein at least 60% of the R units are phosphonate units and 40% of the R units are hydrogen. In a still further embodiment of this aspect, the chromogenic polymers comprise a mixture of R units wherein at least 50% of the R units are phosphonate units and 50% of the R units are hydrogen.

Another aspect relates to chromogenic polymers that comprise a mixture of carboxylate and sulfonate units. In one embodiment of this aspect, the chromogenic polymers comprise a mixture of R units wherein at least 90% of the R units are carboxylate units and 10% of the R units are sulfonate. In another embodiment of this aspect, the chromogenic polymers comprise a mixture of R units wherein at least 80% of the R units are carboxylate units and 20% of the R units are sulfonate. In a further embodiment of this aspect, the chromogenic polymers comprise a mixture of R units wherein at least 70% of the R units are carboxylate units and 30% of the R units are sulfonate. In a yet further embodiment of this aspect, the chromogenic polymers comprise a mixture of R units wherein at least 60% of the R units are carboxylate units and 40% of the R units are sulfonate. In a still further embodiment of this aspect, the chromogenic polymers comprise a mixture of R units wherein at least 50% of the R units are carboxylate units and 50% of the R units are sulfonate.

$R^1$ Units $R^1$ units are moieties that can interact with the disclosed biogenic amines or $R^1$ units can provide improved organic phase or water phase solubility for the chromogenic polymers. $R^1$ units are independently chosen from one another. $R^1$ units when taken together with $L^1$ linking units can modify the hydrophilic or hydrophobic character of the chromogenic polymers.

In one aspect, $R^1$ units can complex with the one or more substrate recognition elements and thereby further enhance the ability of the chromogenic polymers to differentiate between different biogenic amines. When $R^1$ units are the same or a different anionic moiety, for example, a carboxylate moiety, the $L^1$ linking group is different than the L linking group present for R units.

One aspect of $R^1$ units relates to units that modify the hydrophilic character of the polymers. In one embodiment, $R^1$ is hydrogen and $R^1$ is taken together with an $L^1$ unit comprising a polyalkyleneoxy unit as further described herein. In another embodiment, $R^1$ is hydroxyl and $R^1$ is taken together with an $L^1$ unit comprising a polyalkyleneoxy unit as further described herein. In a further embodiment, $R^1$ is methoxy and $R^1$ is taken together with an $L^1$ unit comprising a polyalkyleneoxy unit as further described herein.

Another aspect of $R^1$ units relates to units that modify the hydrophobic character of the polymers. In one embodiment, $R^1$ is hydrogen and $R^1$ is taken together with an $L^1$ unit comprising a polyalkylene unit as further described herein.

$R^2$ Units $R^2$ units are moieties that interact with the disclosed biogenic amines. $R^2$ units are independently chosen from one another. $R^2$ units serve as a moiety that complexes with the one or more substrate recognition elements and therefore serve to differentiate between different biogenic amines. Non-limiting examples of $R^2$ units include:

i) —H;
ii) —OM;
iii) —CO$_2$M;
iv) —SO$_3$M;
v) —PO$_3$M$_2$; and
vi) —OCH$_3$;

wherein M is hydrogen, an alkali metal, an alkali earth metal, a transition metal, or mixtures thereof as defined herein above.

In one aspect of the disclosed chromogenic polymers, $R^2$ units comprise a carboxylate unit. Non-limiting examples of this aspect of $R^2$ units include:

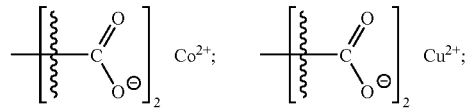

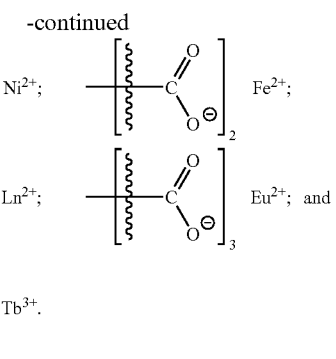

In another aspect of the disclosed chromogenic polymers, $R^2$ units comprise a sulfonate unit. Non-limiting examples of this aspect of $R^2$ units include:

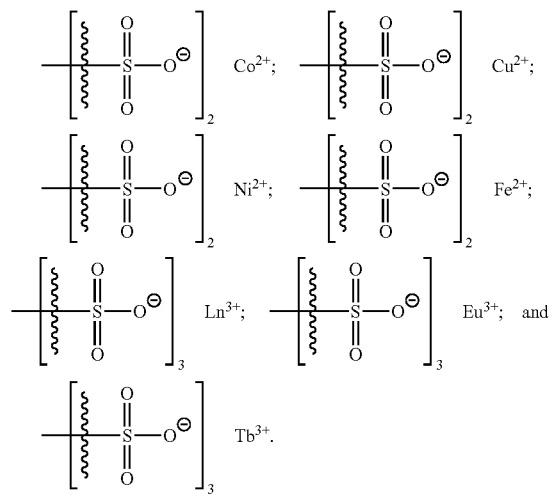

In a further aspect of the disclosed chromogenic polymers, $R^2$ units comprise a phosphonate unit. Non-limiting examples of this aspect of $R^2$ units include:

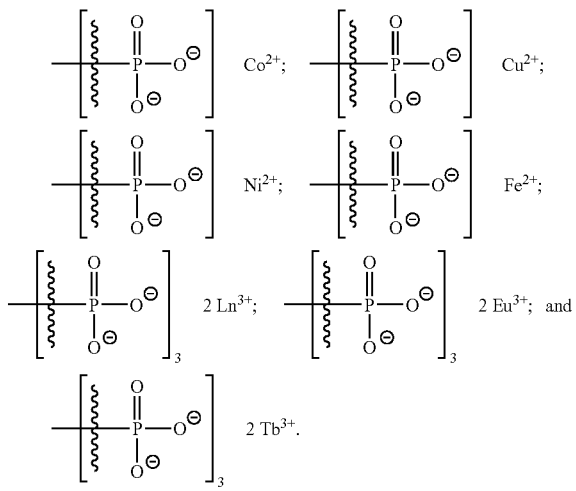

In a yet further aspect of the disclosed chromogenic polymers, $R^2$ units are an admixture of charged units and non-charged units. In one embodiment of this aspect, the chromogenic polymers comprise a mixture of $R^2$ units wherein at least 90% of the R units are carboxylate units and 10% of the $R^2$ units are hydrogen. In another embodiment of this aspect, the chromogenic polymers comprise a mixture of $R^2$ units wherein at least 80% of the $R^2$ units are carboxylate units and 20% of the $R^2$ units are hydrogen. In a further embodiment of this aspect, the chromogenic polymers comprise a mixture of $R^2$ units wherein at least 70% of the $R^2$ units are carboxylate units and 30% of the $R^2$ units are hydrogen. In a yet further embodiment of this aspect, the chromogenic polymers comprise a mixture of $R^2$ units wherein at least 60% of the $R^2$ units are carboxylate units and 40% of the $R^2$ units are hydrogen. In a still further embodiment of this aspect, the chromogenic polymers comprise a mixture of $R^2$ units wherein at least 50% of the R units are carboxylate units and 50% of the $R^2$ units are hydrogen.

In a further embodiment of this aspect, the chromogenic polymers comprise a mixture of $R^2$ units wherein at least 90% of the $R^2$ units are sulfonate units and 10% of the $R^2$ units are hydrogen. In another embodiment of this aspect, the chromogenic polymers comprise a mixture of $R^2$ units wherein at least 80% of the $R^2$ units are sulfonate units and 20% of the $R^2$ units are hydrogen. In a further embodiment of this aspect, the chromogenic polymers comprise a mixture of $R^2$ units wherein at least 70% of the $R^2$ units are sulfonate units and 30% of the $R^2$ units are hydrogen. In a yet further embodiment of this aspect, the chromogenic polymers comprise a mixture of $R^2$ units wherein at least 60% of the $R^2$ units are sulfonate units and 40% of the $R^2$ units are hydrogen. In a still further embodiment of this aspect, the chromogenic polymers comprise a mixture of $R^2$ units wherein at least 50% of the $R^2$ units are sulfonate units and 50% of the $R^2$ units are hydrogen.

In a yet further embodiment of this aspect, the chromogenic polymers comprise a mixture of $R^2$ units wherein at least 90% of the $R^2$ units are phosphonate units and 10% of the $R^2$ units are hydrogen. In another embodiment of this aspect, the chromogenic polymers comprise a mixture of $R^2$ units wherein at least 80% of the $R^2$ units are phosphonate units and 20% of the $R^2$ units are hydrogen. In a further embodiment of this aspect, the chromogenic polymers comprise a mixture of $R^2$ units wherein at least 70% of the $R^2$ units are phosphonate units and 30% of the $R^2$ units are hydrogen. In a yet further embodiment of this aspect, the chromogenic polymers comprise a mixture of $R^2$ units wherein at least 60% of the $R^2$ units are phosphonate units and 40% of the $R^2$ units are hydrogen. In a still further embodiment of this aspect, the chromogenic polymers comprise a mixture of $R^2$ units wherein at least 50% of the $R^2$ units are phosphonate units and 50% of the $R^2$ units are hydrogen.

Another aspect relates to chromogenic polymers that comprise a mixture of carboxylate and sulfonate units. In one embodiment of this aspect, the chromogenic polymers comprise a mixture of $R^2$ units wherein at least 90% of the $R^2$ units are carboxylate units and 10% of the $R^2$ units are sulfonate. In another embodiment of this aspect, the chromogenic polymers comprise a mixture of $R^2$ units wherein at least 80% of the $R^2$ units are carboxylate units and 20% of the R units are sulfonate. In a further embodiment of this aspect, the chromogenic polymers comprise a mixture of $R^2$ units wherein at least 70% of the $R^2$ units are carboxylate units and 30% of the $R^2$ units are sulfonate. In a yet further embodiment of this aspect, the chromogenic polymers comprise a mixture of $R^2$ units wherein at least 60% of the $R^2$ units are carboxylate units and 40% of the $R^2$ units are sulfonate. In a still further embodiment of this aspect, the chromogenic polymers comprise a mixture of $R^2$ units wherein at least 50% of the $R^2$ units are carboxylate units and 50% of the $R^2$ units are sulfonate.

$R^3$ and $R^4$ Units $R^3$ and $R^4$ units are moieties that interact with the disclosed biogenic amines. $R^3$ and $R^4$ units are independently chosen from one another. $R^3$ and $R^4$ units serve as a moiety that complexes with the one or more substrate recognition elements and therefore serve to differentiate between different biogenic amines. Non-limiting examples of $R^3$ and $R^4$ units include:

i) —H;
ii) —OM;
iii) —$CO_2M$;
iv) —$SO_3M$;
v) —$PO_3M_2$; and
vi) —$OCH_3$;

wherein M is hydrogen, an alkali metal, an alkali earth metal, a transition metal, or mixtures thereof as defined herein above.

In one aspect of the disclosed chromogenic polymers, $R^3$ and $R^4$ units comprise a carboxylate unit. Non-limiting examples of this aspect of $R^3$ and $R^4$ units include:

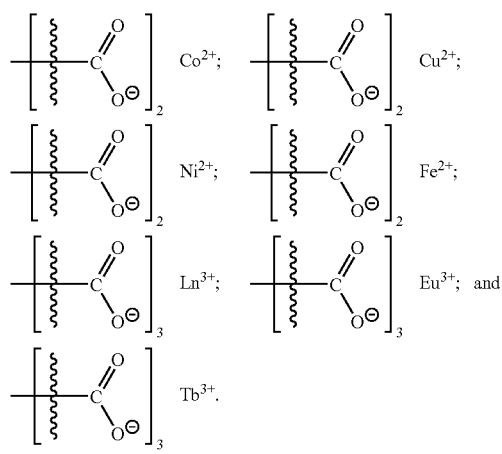

In another aspect of the disclosed chromogenic polymers, $R^3$ and $R^4$ units comprise a sulfonate unit. Non-limiting examples of this aspect of $R^3$ and $R^4$ units include:

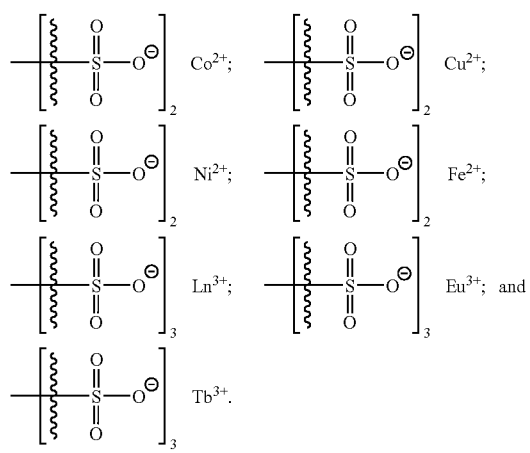

In a further aspect of the disclosed chromogenic polymers, $R^3$ and $R^4$ units comprise a phosphonate unit. Non-limiting examples of this aspect of $R^3$ and $R^4$ units include:

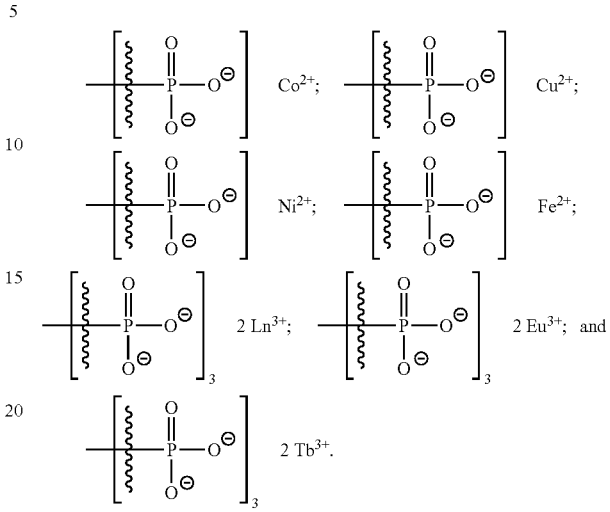

In a yet further aspect of the disclosed chromogenic polymers, $R^3$ and $R^4$ units are an admixture of charged and non-charged units. In one embodiment of this aspect, the chromogenic polymers comprise a mixture of $R^3$ and $R^4$ units wherein at least 90% of the $R^3$ and $R^4$ units are carboxylate and 10% of the $R^3$ and $R^4$ units are hydrogen. In another embodiment of this aspect, the chromogenic polymers comprise a mixture of $R^3$ and $R^4$ units wherein at least 80% of the $R^3$ and $R^4$ units are carboxylate and 20% of the $R^3$ and $R^4$ units are hydrogen. In a further embodiment of this aspect, the chromogenic polymers comprise a mixture of $R^3$ and $R^4$ units wherein at least 70% of the $R^3$ and $R^4$ units are carboxylate and 30% of the $R^3$ and $R^4$ units are hydrogen. In a yet further embodiment of this aspect, the chromogenic polymers comprise a mixture of $R^3$ and $R^4$ units wherein at least 60% of the $R^3$ and $R^4$ units are carboxylate and 40% of the $R^3$ and $R^4$ units are hydrogen. In a still further embodiment of this aspect, the chromogenic polymers comprise a mixture of $R^3$ and $R^4$ units wherein at least 50% of the $R^3$ and $R^4$ units are carboxylate and 50% of the $R^3$ and $R^4$ units are hydrogen.

In a further embodiment of this aspect, the chromogenic polymers comprise a mixture of $R^3$ and $R^4$ units wherein at least 90% of the $R^3$ and $R^4$ units are sulfonate and 10% of the $R^3$ and $R^4$ units are hydrogen. In another embodiment of this aspect, the chromogenic polymers comprise a mixture of $R^3$ and $R^4$ units wherein at least 80% of the $R^3$ and $R^4$ units are sulfonate and 20% of the $R^3$ and $R^4$ units are hydrogen. In a further embodiment of this aspect, the chromogenic polymers comprise a mixture of $R^3$ and $R^4$ units wherein at least 70% of the $R^3$ and $R^4$ units are sulfonate and 30% of the $R^3$ and $R^4$ units are hydrogen. In a yet further embodiment of this aspect, the chromogenic polymers comprise a mixture of $R^3$ and $R^4$ units wherein at least 60% of the $R^3$ and $R^4$ units are sulfonate and 40% of the $R^3$ and $R^4$ units are hydrogen. In a still further embodiment of this aspect, the chromogenic polymers comprise a mixture of $R^3$ and $R^4$ units wherein at least 50% of the $R^3$ and $R^4$ units are sulfonate and 50% of the $R^3$ and $R^4$ units are hydrogen.

In a yet further embodiment of this aspect, the chromogenic polymers comprise a mixture of $R^3$ and $R^4$ units wherein at least 90% of the $R^3$ and $R^4$ units are phosphonate and 10% of the $R^3$ and $R^4$ units are hydrogen. In another embodiment of this aspect, the chromogenic polymers comprise a mixture of $R^3$ and $R^4$ units wherein at least 80% of the $R^3$ and $R^4$ units are phosphonate and 20% of the $R^3$ and $R^4$ units are hydrogen. In a further embodiment of this aspect, the chromogenic polymers comprise a mixture of $R^3$ and $R^4$ units wherein at least 70% of the $R^3$ and $R^4$ units are phosphonate and 30% of the $R^3$ and $R^4$ units are hydrogen. In a yet further embodiment of this aspect, the chromogenic polymers comprise a mixture of $R^3$ and $R^4$ units wherein at least 60% of the $R^3$ and $R^4$ units are phosphonate and 40% of the $R^3$ and $R^4$ units are hydrogen. In a still further embodiment of this aspect, the chromogenic polymers comprise a mixture of $R^3$ and $R^4$ units wherein at least 50% of the $R^3$ and $R^4$ units are phosphonate and 50% of the $R^3$ and $R^4$ units are hydrogen.

Another aspect relates to chromogenic polymers wherein $R^3$ and $R^4$ units are taken together with the two phenyl rings to form a fused ring having from 5 to 7 carbon atoms that comprise a mixture of carboxylate and sulfonate units. A non-limiting embodiment of this aspect relates to $R^3$ and $R^4$ units taken together when the index z is equal to 0 and therefore $L^5$ is absent, to form a 5-member ring, thereby forming a fluorenyl group having the formula:

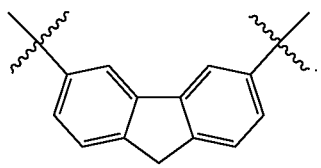 [SMILES: *c1ccc2c(c1)-c1cc(*)ccc1C2]

Linking Units L, $L^1$, $L^3$, and $L^4$

Linking units L, $L^1$, $L^3$, and $L^4$ are each independently chosen from:
i) $-(CR^{5a}R^{5b})_m-$; or
ii) $-(CR^{5a}R^{5b})_m[O(CR^{5a}R^{5b})_m]_k-$;
wherein $R^{5a}$ and $R^{5b}$ are each independently hydrogen or methyl; the index k is an integer from 1 to 20; and the index m is an integer from 0 to 10.

A first category of L, $L^1$, $L^3$, and $L^4$ linking units relates to alkylene units having the formula:

$-(CH_2)_m-$ wherein $R^{5a}$ and $R^{5b}$ are each hydrogen; and the index m is from 1 to 10. Non-limiting examples of this category include:
i) $-CH_2-$;
ii) $-CH_2CH_2-$;
iii) $-CH_2CH_2CH_2-$;
iv) $-CH_2CH_2CH_2CH_2-$;
v) $-CH_2CH_2CH_2CH_2CH_2-$;
vi) $-CH_2CH_2CH_2CH_2CH_2CH_2-$;
vii) $-CH_2CH_2CH_2CH_2CH_2CH_2CH_2-$;
viii) $-CH_2CH_2CH_2CH_2CH_2CH_2CH_2CH_2-$;
ix) $-CH_2CH_2CH_2CH_2CH_2CH_2CH_2CH_2CH_2-$; and
x) $-CH_2CH_2CH_2CH_2CH_2CH_2CH_2CH_2CH_2CH_2-$.

One embodiment of this category relates to chromogenic polymers comprising an L unit having the formula:
i) $-CH_2CH_2-$;
ii) $-CH_2CH_2CH_2-$; or
iii) $-CH_2CH_2CH_2CH_2-$.

Another category of L, $L^1$, $L^3$, and $L^4$ linking units relates to alkylene units having the formula:

$-[CH_2CH(CH_3)]_m-$ or $-[CH(CH_3)CH_2]_m-$ wherein $R^{5a}$ and $R^{5b}$ are each hydrogen or methyl; and the index m is from 1 to 10. Non-limiting examples of this category include:

i) $-CH_2CH(CH_3)-$;
ii) $-CH(CH_3)CH_2-$;
iii) $-CH(CH_3)CH_2CH_2CH(CH_3)-$;
iv) $-CH_2CH(CH_3)CH_2CH(CH_3)-$;
v) $-CH(CH_3)CH_2CH(CH_3)CH_2-$;
vi) $-CH_2CH(CH_3)CH(CH_3)CH_2-$;
vii) $-CH(CH_3)CH_2CH_2CH(CH_3)CH_2CH(CH_3)-$;
viii) $-CH_2CH(CH_3)CH_2CH(CH_3)CH_2CH(CH_3)-$;
ix) $-CH(CH_3)CH_2CH(CH_3)CH_2CH_2CH(CH_3)-$;
x) $-CH_2CH(CH_3)CH(CH_3)CH_2CH_2CH(CH_3)-$;
a. $-CH(CH_3)CH_2CH_2CH(CH_3)CH(CH_3)CH_2-$;
b. $-CH_2CH(CH_3)CH_2CH(CH_3)CH(CH_3)CH_2-$;
xi) $-CH(CH_3)CH_2CH(CH_3)CH_2CH(CH_3)CH_2-$; and
xii) $-CH_2CH(CH_3)CH(CH_3)CH_2CH(CH_3)CH_2-$.

A further category of L, $L^1$, $L^3$, and $L^4$ linking units relates to alkyleneoxy units having the formula:

$-(CR^{5a}R^{5b})_m[O(CR^{5a}R^{5b})_m]_k-$ wherein the index k is an integer from 1 to 20 and the index m is an integer from 1 to 10. Non-limiting examples of this category of L, $L^1$, $L^3$, and $L^4$ linking units includes units chosen from:
i) $-(CH_2CH_2)[O(CH_2CH_2)]O-$;
ii) $-(CH_2CH_2)[O(CH_2CH_2)]_2O-$;
iii) $-(CH_2CH_2)[O(CH_2CH_2)]_3O-$;
iv) $-(CH_2CH_2)[O(CH_2CH_2)]_4O-$;
v) $-(CH_2CH_2)[O(CH_2CH_2)]_5O-$;
vi) $-(CH_2CH_2)[O(CH_2CH_2)]_6O-$;
vii) $-(CH_2CH_2)[O(CH_2CH_2)]_7O-$;
viii) $-(CH_2CH_2)[O(CH_2CH_2)]_8O-$; and
ix) $-(CH_2CH_2)[O(CH_2CH_2)]_9O-$.

$L^2$ and $L^5$ Linking Units $L^2$ and $L^5$ units are backbone linking units that can be present when the index z is equal to 1 or absent when the index z is equal to 0. $L^5$ linking units are chosen from:
i) i) $-(CR^{5a}R^{5b})_j(CH=CH)(CR^{5a}R^{5b})_j-$;
ii) $-(CR^{5a}R^{5b})_j(C\equiv C)(CR^{5a}R^{5b})_j-$;
$R^{5a}$ and $R^{5b}$ are each independently hydrogen or methyl; the index j is an integer from 0 to 10.

One category of $L^2$ and $L^5$ units relates to chromogenic polymers having an alkynyl linking unit. Non-limiting examples of polymer units comprising an alkynyl linking group include:

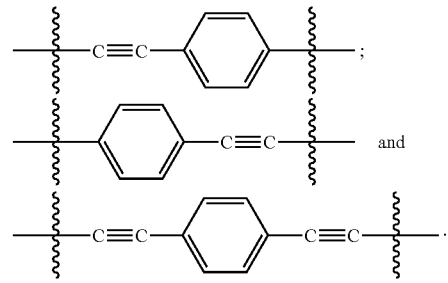

Another category of $L^5$ units relates to chromogenic polymers having an alkenyl linking unit. Non-limiting examples of polymer units comprising an alkenyl linking group include:

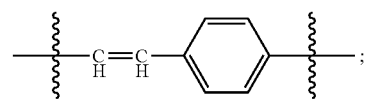

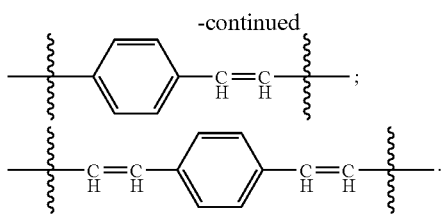

One category of chromogenic polymers relates to poly(thiophene)s having the formula:

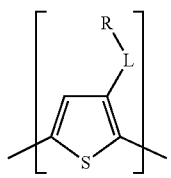

wherein R is independently chosen from:
i) —$CO_2M$;
ii) —$SO_3M$; and
iii) —$PO_3M_2$;

M is a substrate recognition element, and L is linking unit having from 1 to 10 methylene units.

One aspect of this category relates to chromogenic polymers comprising a poly(thiophene) backbone having the formula:

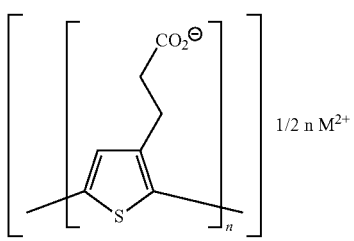

wherein the index n has a value such that the chromogenic polymer has an average molecular weight of from about 1,000 Da to about 20,000 Da, and M is chosen from copper, cobalt, or nickel.

One embodiment of this aspect relates to chromogenic polymers having an average molecular weight of from about 1,000 Da to about 20,000 Da. and wherein M is copper. An iteration of this embodiment is a chromogenic polymer having an average molecular weight of from about 1,000 Da to about 5,000 Da. Another iteration of this embodiment is a chromogenic polymer having an average molecular weight of from about 2,000 Da to about 6,000 Da. A further iteration of this embodiment is a chromogenic polymer having an average molecular weight of from about 3,000 Da to about 7,000 Da. A yet further iteration of this embodiment is a chromogenic polymer having an average molecular weight of from about 4,000 Da to about 8,000 Da. A still further iteration of this embodiment is a chromogenic polymer having an average molecular weight of from about 5,000 Da to about 9,000 Da.

Another aspect relates to chromogenic polymers having a backbone comprising units having the formula:

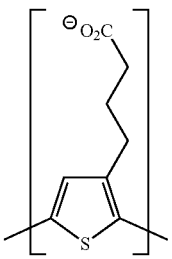

wherein the chromogenic polymer has an average molecular weight of from about 1,000 Da to about 20,000 Da. One embodiment of this aspect relates to chromogenic polymers having an average molecular weight of from about 1,000 Da to about 20,000 Da. and wherein the recognition element associated therewith can be copper, cobalt, nickel, and the like. An iteration of this embodiment is a chromogenic polymer having an average molecular weight of from about 1,000 Da to about 5,000 Da. Another iteration of this embodiment is a chromogenic polymer having an average molecular weight of from about 2,000 Da to about 6,000 Da. A further iteration of this embodiment is a chromogenic polymer having an average molecular weight of from about 3,000 Da to about 7,000 Da. A yet further iteration of this embodiment is a chromogenic polymer having an average molecular weight of from about 4,000 Da to about 8,000 Da. A still further iteration of this embodiment is a chromogenic polymer having an average molecular weight of from about 5,000 Da to about 9,000 Da.

Another aspect relates to chromogenic polymers having a backbone comprising units having the formula:

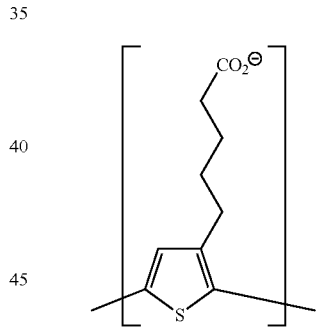

wherein the chromogenic polymer has an average molecular weight of from about 1,000 Da to about 20,000 Da. One embodiment of this aspect relates to chromogenic polymers having an average molecular weight of from about 1,000 Da to about 20,000 Da. and wherein the recognition element associated therewith can be copper, cobalt, nickel, and the like. An iteration of this embodiment is a chromogenic polymer having an average molecular weight of from about 1,000 Da to about 5,000 Da. Another iteration of this embodiment is a chromogenic polymer having an average molecular weight of from about 2,000 Da to about 6,000 Da. A further iteration of this embodiment is a chromogenic polymer having an average molecular weight of from about 3,000 Da to about 7,000 Da. A yet further iteration of this embodiment is a chromogenic polymer having an average molecular weight of from about 4,000 Da to about 8,000 Da. A still further iteration of this embodiment is a chromogenic polymer having an average molecular weight of from about 5,000 Da to about 9,000 Da.

A yet another aspect of this category relates to chromogenic polymers comprising a poly(thiophene) backbone having the formula:

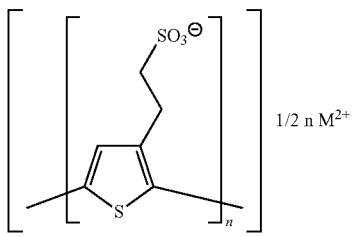

wherein the index n has a value such that the chromogenic polymer has an average molecular weight of from about 1,000 Da to about 20,000 Da, and M is chosen from copper, cobalt, or nickel.

One embodiment of this aspect relates to chromogenic polymers having an average molecular weight of from about 1,000 Da to about 20,000 Da. and wherein M is copper. An iteration of this embodiment is a chromogenic polymer having an average molecular weight of from about 1,000 Da to about 5,000 Da. Another iteration of this embodiment is a chromogenic polymer having an average molecular weight of from about 2,000 Da to about 6,000 Da. A further iteration of this embodiment is a chromogenic polymer having an average molecular weight of from about 3,000 Da to about 7,000 Da. A yet further iteration of this embodiment is a chromogenic polymer having an average molecular weight of from about 4,000 Da to about 8,000 Da. A still further iteration of this embodiment is a chromogenic polymer having an average molecular weight of from about 5,000 Da to about 9,000 Da.

Another category of chromogenic polymers relates to poly(thiophene)s having the formula:

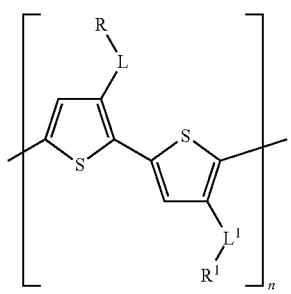

wherein R is independently chosen from:
i) —$CO_2M$;
ii) —$SO_3M$; and
iii) —$PO_3M_2$;
$R^1$ is hydrogen or methoxy;
L has the formula —$(CH_2)_m$—, the index m is an integer from 1 to 10; $L^1$ has the formula —$(CH_2)_m$— or —$(CH_2)_m[O(CH_2)_m]_k$—; the index k is an integer from 1 to 20, the index m is an integer from 1 to 10; M is a substrate recognition element.

One aspect of this category relates to chromogenic polymers wherein $L^1$ and $R^1$ together provide a unit that enhances the solubility of the polymers in hydrophobic systems, inter alia, organic solvents. One non-limiting example of a backbone according to this aspect has the formula:

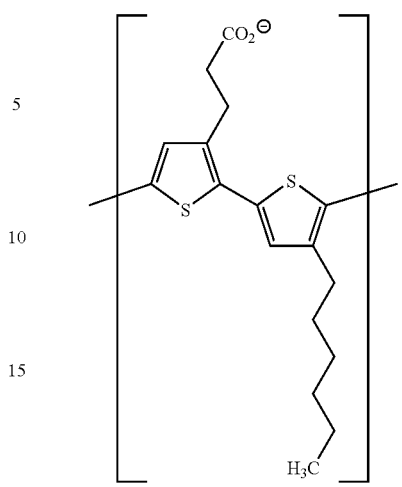

Another aspect of this category relates to chromogenic polymers wherein $L^1$ and $R^1$ together provide a unit that enhances the solubility of the polymers in hydrophilic systems, inter alia, aqueous systems. One non-limiting example of a backbone according to this aspect has the formula:

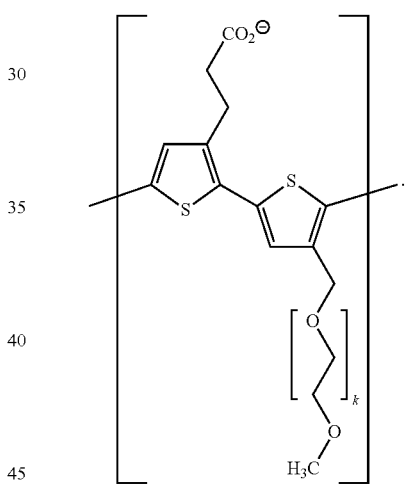

Another category of chromogenic polymers relates to random poly(thiophene) copolymer having, for example, the formula:

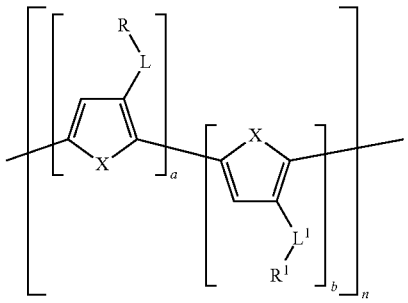

wherein the indices a+b=n.

A yet further category of chromogenic polymers relates to poly(furan)s having the formula:

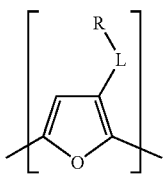

wherein R is independently chosen from:
  i) —CO₂M;
  ii) —SO₃M; and
  iii) —PO₃M₂;
M is a substrate recognition element, and L is linking unit having from 1 to 10 methylene units.

One aspect of this category relates to chromogenic polymers comprising a poly(thiophene) backbone having the formula:

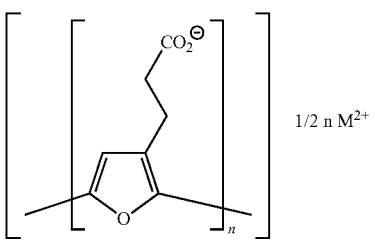

wherein the index n has a value such that the chromogenic polymer has an average molecular weight of from about 1,000 Da to about 20,000 Da, and M is chosen from copper, cobalt, or nickel.

One embodiment of this aspect relates to chromogenic polymers having an average molecular weight of from about 1,000 Da to about 20,000 Da. and wherein the recognition element associated therewith can be copper, cobalt, nickel, and the like. An iteration of this embodiment is a chromogenic polymer having an average molecular weight of from about 1,000 Da to about 5,000 Da. Another iteration of this embodiment is a chromogenic polymer having an average molecular weight of from about 2,000 Da to about 6,000 Da. A further iteration of this embodiment is a chromogenic polymer having an average molecular weight of from about 3,000 Da to about 7,000 Da. A yet further iteration of this embodiment is a chromogenic polymer having an average molecular weight of from about 4,000 Da to about 8,000 Da. A still further iteration of this embodiment is a chromogenic polymer having an average molecular weight of from about 5,000 Da to about 9,000 Da.

Another aspect relates to chromogenic polymers having a backbone comprising units having the formula:

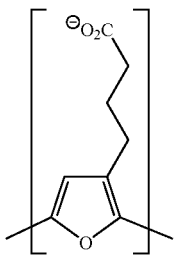

wherein the chromogenic polymer has an average molecular weight of from about 1,000 Da to about 20,000 Da. One embodiment of this aspect relates to chromogenic polymers having an average molecular weight of from about 1,000 Da to about 20,000 Da. and wherein the recognition element associated therewith can be copper, cobalt, nickel, and the like. An iteration of this embodiment is a chromogenic polymer having an average molecular weight of from about 1,000 Da to about 5,000 Da. Another iteration of this embodiment is a chromogenic polymer having an average molecular weight of from about 2,000 Da to about 6,000 Da. A further iteration of this embodiment is a chromogenic polymer having an average molecular weight of from about 3,000 Da to about 7,000 Da. A yet further iteration of this embodiment is a chromogenic polymer having an average molecular weight of from about 4,000 Da to about 8,000 Da. A still further iteration of this embodiment is a chromogenic polymer having an average molecular weight of from about 5,000 Da to about 9,000 Da.

A still further category of chromogenic polymers relates to poly(pyrrole)s having the formula:

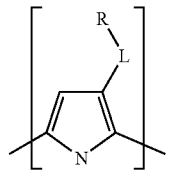

wherein R is independently chosen from:
  i) —CO₂M;
  ii) —SO₃M; and
  iii) —PO₃M₂;
M is a substrate recognition element, and L is linking unit having from 1 to 10 methylene units.

One aspect of this category relates to chromogenic polymers comprising a poly(thiophene) backbone having the formula:

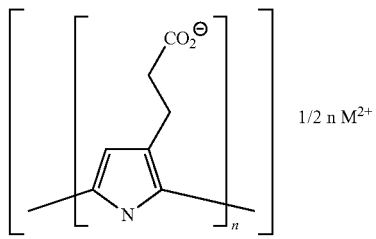

wherein the index n has a value such that the chromogenic polymer has an average molecular weight of from about 1,000 Da to about 20,000 Da, and M is chosen from copper, cobalt, or nickel.

One embodiment of this aspect relates to chromogenic polymers having an average molecular weight of from about 1,000 Da to about 20,000 Da. and wherein the recognition element associated therewith can be copper, cobalt, nickel, and the like. An iteration of this embodiment is a chromogenic polymer having an average molecular weight of from about 1,000 Da to about 5,000 Da. Another iteration of this embodiment is a chromogenic polymer having an average molecular weight of from about 2,000 Da to about 6,000 Da. A further iteration of this embodiment is a chromogenic polymer having an average molecular weight of from about 3,000 Da to about 7,000 Da. A yet further iteration of this embodiment is a chromogenic polymer having an average molecular weight of from about 4,000 Da to about 8,000 Da. A still further iteration of this embodiment is a chromogenic polymer having an average molecular weight of from about 5,000 Da to about 9,000 Da.

Another aspect relates to chromogenic polymers having a backbone comprising units having the formula:

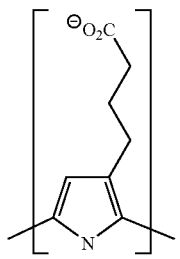

wherein the chromogenic polymer has an average molecular weight of from about 1,000 Da to about 20,000 Da. One embodiment of this aspect relates to chromogenic polymers having an average molecular weight of from about 1,000 Da to about 20,000 Da. and wherein the recognition element associated therewith can be copper, cobalt, nickel, and the like. An iteration of this embodiment is a chromogenic polymer having an average molecular weight of from about 1,000 Da to about 5,000 Da. Another iteration of this embodiment is a chromogenic polymer having an average molecular weight of from about 2,000 Da to about 6,000 Da. A further iteration of this embodiment is a chromogenic polymer having an average molecular weight of from about 3,000 Da to about 7,000 Da. A yet further iteration of this embodiment is a chromogenic polymer having an average molecular weight of from about 4,000 Da to about 8,000 Da. A still further iteration of this embodiment is a chromogenic polymer having an average molecular weight of from about 5,000 Da to about 9,000 Da.

The preparation of the disclosed chromogenic polymer can be carried out using methods known in the art or other methods disclosed herein. As one of skill in the art will readily recognize, synthetic polymer procedures can be readily modified to produce varying polymer chain lengths without undue experimentation (e.g., shortening or lengthening a polymerization reaction time). HT-poly(3-(2-(4,5-dihydro-4,4-dimethyl-2-oxazolyl)ethyl)thiophene was synthesized using methods disclosed by McCullough as described in the examples herein, for example, using Gronowitz conditions for the formation of dimers, as described by Ewbank et al. (Ewbank, P. C et al., *Tetrahedron* 2004, 60, 11269-11275).

EXAMPLE 1

HT-2,5-poly(3-(2-(4,5-dihydro-4,4 dimethyl-2-oxazolyl)ethyl)thiophene 2-(2-(2-bromo-5-(trimethylstannyl)thiophen-3-yl)ethyl)-4,5-dihydro-4,4-dimethyloxazol (7.0 g, 15.5 mmol) was weighed in 100 mL Schlenk flask followed by the addition of 30 mL dry DMF then purged with nitrogen for 15 min. To this mixture, copper (II) oxide (1.24 g, 15.5 mmol, 1 eq.), triphenylphosphine (814 mg, 0.031 mmol, 0.20 eq.) and bis(dibenzylidene acetone)palladium(0) (446 mg, 0.776 mmol, 0.05 eq) was added all at once. The greenish-brown suspension solution was purged with nitrogen for 15 min then heated to 100° C. and stirred for 18 hrs under argon atmosphere. The reaction mixture was filtered thru celite and the purple precipitate was extracted with chloroform. The chloroform extract was concentrated and the resulting solid was soxhlet-extracted with hexanes then extracted with chloroform. The solvent was removed to afford a purple solid (2.1 g, 66% S5 yield). $^1$H NMR (300 MHz, CDCl$_3$): δ=7.06 (s, 1H), 3.94 (s, 2H), 3.14 (d, 2H), 2.66 (d, 2H), 1.28 (s, 6H); $^{13}$C NMR (75 MHz, CDCl$_3$): δ=166.7, 138.4, 134.4, 132.4, 129.8, 80.0, 68.0, 29.6, 29.2, 26.4. CDCl$_3$

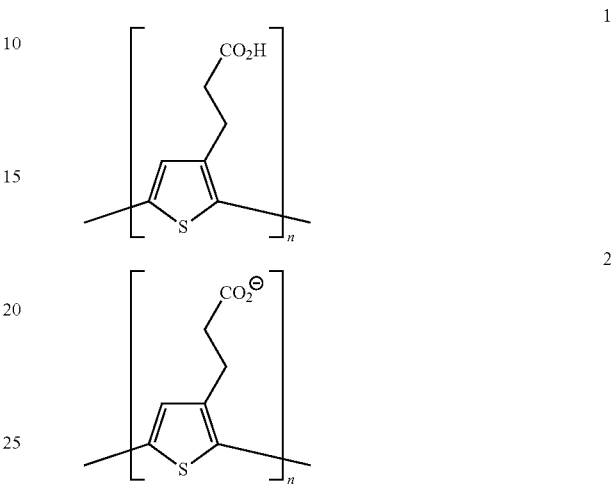

HT-poly(thiophene-3-propionoic acid) (1), and HT-poly (thiophene-3-propionate) (2) have been reported by McCullough. For example, polymer 1 can be prepared by Stille/CuO polymerization of an oxazoline protected monomer followed by acid hydrolysis according to the method of McCullough et al. Polymer 1 can be deprotonated to form 2, a salt, by exposing 1 to an appropriate base (McCullough, R. D.; Ewbank, P. C.; Loewe, R. S. *J. Am. Chem. Soc.* 1997, 119, 633-634). A representative, exemplary procedure for the synthesis of polymer 1 is given herein below.

Polymer (1). HT-2,5-poly(3-(2-(4,5-dihydro-4,4 dimethyl-2-oxazolyl)ethyl)thiophene (1.9 g, 10.1 mmol) was dissolved in 50 mL chloroform then 50 mL 3 N HCl was added to the mixture. The reaction was refluxed overnight. The resulting dark purple polymer was filtered, washed with water and chloroform and dried to give the product (1.05 g, 67% yield). $^1$H NMR (300 MHz, CD$_3$OD) (characterized as the cesium salt): δ=7.16 (s, 1H), 3.11 (t, 2H), 2.54 (t, 2H). Molecular weights and distribution of polymer 1 were determined as the butyl ester using MALDI-TOF MS. The ester was obtained by acid-catalyzed esterification of polymer 5 with sulfuric acid in refluxing n-butanol. $^1$H NMR (300 MHz, CDCl$_3$): δ=7.02 (s, 1H), 4.11 (t, 2H), 3.14 (t, 2H), 2.70 (t, 2H), 1.62 (m, 2H), 1.35 (m, 2H), 0.92 (t, 3H); MALDITOF MS: $M_n$=3170, $M_w$=3230, PDI=1.02.

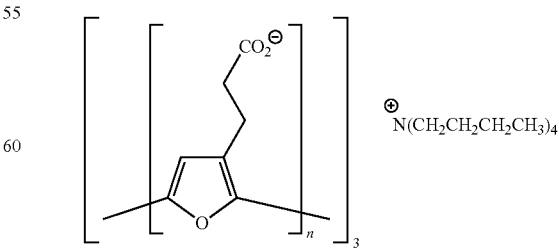

The tetrabutylammonium polymer 3 can be prepared by adding polymer 1 to deionized water followed by the addition of an aliquot of 40% (w/v) tetrabutylammonium hydroxide solution. The pH of a polymer solution can be adjusted to an appropriate pH using acid or base (e.g., hydrochloric acid or sodium hydroxide).

METHODS

Disclosed herein are methods for detecting the presence of a biogenic amine, comprising:
 a) providing a chromogenic-responsive polymer;
 b) contacting the polymer in step (a) with an analyte; and
 c) detecting a chromogenic response.
It is understood that the methods disclosed herein can be used in combination with the various chromogenic polymers and compositions disclosed herein, devices, and articles of manufacture, and iterations of both visual and mathematic analysis.
Linear Discriminate Analysis In various aspects, the present invention can use pattern recognition protocols, such as linear discriminate analysis (LDA). LDA of a data set can be carried out using methods known in the art with commercially available software (e.g., Systat, Systat Software, Inc., 2004, Version 11.00.01)
Devices One aspect of the disclosed devices relates to an assay device for determining the presence of one or more biogenic amines, comprising one or more substrates having deposited thereon a chromogenic responsive polymer, as such, disclosed herein are devices suitable for use in sensing applications. The devices disclosed herein can be useful for sensing one or more amines in an analyte. The devices can also be useful for differentiating between different amines that comprise analytes. Methods of using the disclosed devices comprise, in one aspect, identifying an amine from reference data.

In one aspect, devices can comprise a polymeric substrate having a first side and a second side wherein further the chromogenic responsive polymer is deposited onto the first side. The polymeric substrate can comprise one of more suitable polymers, for example, polyethylene, polypropylene, poly(propylene-b-terephthalate), and the like. In another aspect, the devices can comprise a paper having the second side (the side opposite the first side wherein the chromogenic response polymer is applied) comprise a thin metallic film, for example, aluminum. Further aspects and devices are described herein below.

In a further aspect, devices disclosed herein can at least partially detect and/or discriminate between amines. In a specific aspect, the disclosed devices can detect and/or discriminate between diamines. Amines (e.g., diamines) contemplated for use with the disclosed devices can be any amine. Amines can typically be associated with biological and/or bacterial spoilage. As such, the devices disclosed herein can be useful for detecting and/or discriminating between biogenic amines that are released during biological spoilage.

In another aspect, the disclosed devise can be used as a diagnostic tool to detect the quality of protein containing samples. Exemplary protein samples comprise, inter alia, food samples, medical samples, and forensic samples. In a specific aspect, the disclosed devices can be used to detect and/or discriminate between biogenic amines present in, for example, food samples, medical samples, and forensic samples.

Any polymer and/or polymer composition (or combination of more than one polymer or polymer composition) disclosed herein can be used in combination with the herein disclosed devices.

Figure 5:
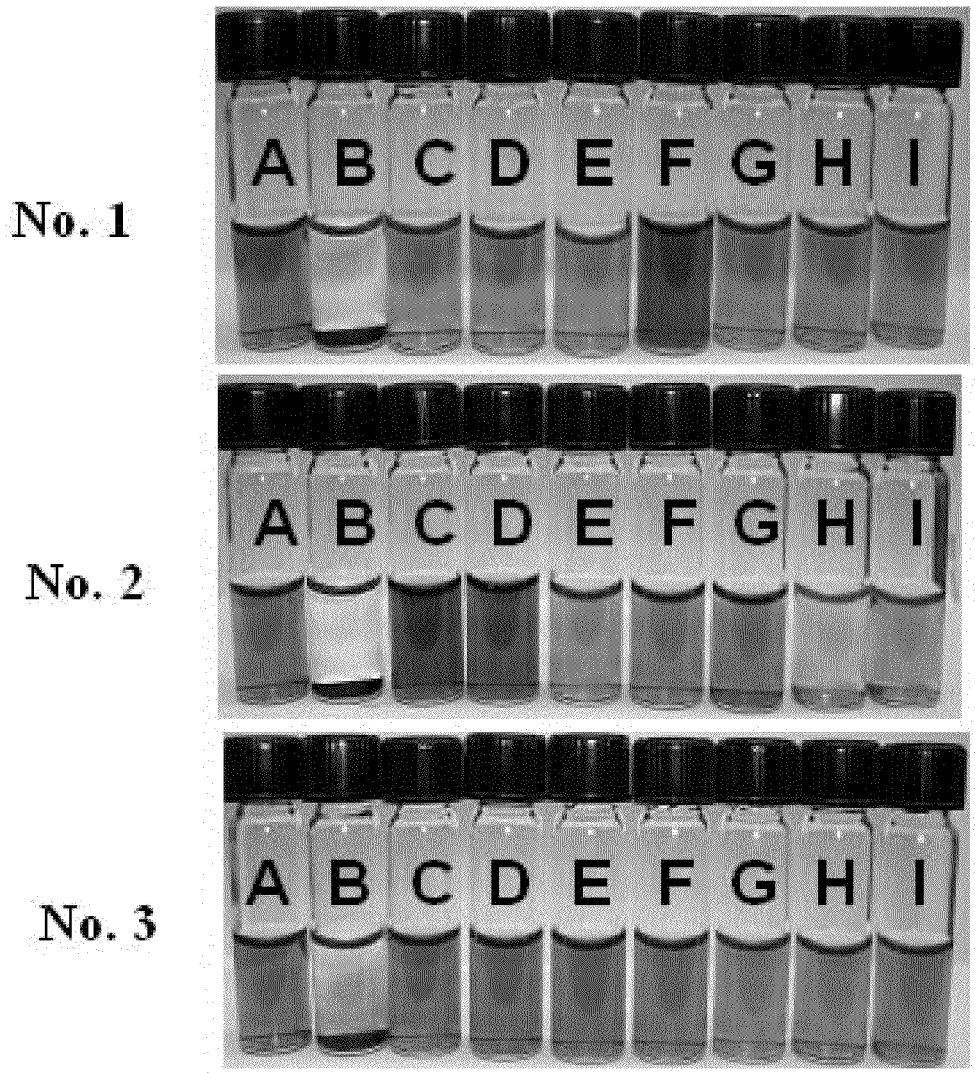
FIG. 5 is a photograph of solutions of polymer 2 with three different substrate recognition elements and the corresponding chromogenic response to a variety of diamines. Series No. 1 comprises $Co^{2+}$, series No. 2 comprises $Cu^{2+}$ and series No. 3 comprises $Ni^{2+}$. Column A: polymer 2 in solution; Column B: polymer 2 with metals as indicated above; Column C: addition of 1,2-ethylenediamine; Column D: addition of 1,3-propylenediamine; Column E: addition of putrescine; Column F: addition of cadaverine; Column G: addition of histamine; Column H: addition of spermidine; Column I: addition of spermine.

FIG. 5 is a photograph of solutions of polymer 2 with three different substrate recognition elements and the corresponding chromogenic response to a variety of diamines. Series No. 1 comprises $Co^{2+}$, series No. 2 comprises $Cu^{2+}$ and series No. 3 comprises $Ni^{2+}$. Vials A-I contain the following:

| | Series No. 1 | | Series No. 2 | | Series No. 3 |
|---|---|---|---|---|---|
| A | polymer 2 | A | polymer 2 | A | polymer 2 |
| B | Polymer 2 + $CoCl_2$ | B | Polymer 2 + $CuCl_2$ | B | Polymer 2 + $NiCl_2$ |
| C | Polymer 2 + $CoCl_2$ + 1,2-ethylene diamine | C | Polymer 2 + $CuCl_2$ + 1,2-ethylene diamine | C | Polymer 2 + $NiCl_2$ + 1,2-ethylene diamine |
| D | Polymer 2 + $CoCl_2$ + 1,3-propylenediamine | D | Polymer 2 + $CuCl_2$ + 1,3-propylenediamine | D | Polymer 2 + $NiCl_2$ + 1,3-propylenediamine |
| E | Polymer 2 + $CoCl_2$ + putrescine | E | Polymer 2 + $CuCl_2$ + putrescine | E | Polymer 2 + $NiCl_2$ + putrescine |
| F | Polymer 2 + $CoCl_2$ + cadaverine | F | Polymer 2 + $CuCl_2$ + cadaverine | F | Polymer 2 + $NiCl_2$ + cadaverine |
| G | Polymer 2 + $CoCl_2$ + histamine | G | Polymer 2 + $CuCl_2$ + histamine | G | Polymer 2 + $NiCl_2$ + histamine |
| H | Polymer 2 + $CoCl_2$ + spermidine | H | Polymer 2 + $CuCl_2$ + spermidine | H | Polymer 2 + $NiCl_2$ + spermidine |
| I | Polymer 2 + $CoCl_2$ + spermine | I | Polymer 2 + $CuCl_2$ + spermine | I | Polymer 2 + $NiCl_2$ + spermine |

As depicted in FIG. 5, the chromogenic response for each sample is dependent on both the substrate recognition element and biogenic amine.

Figure 6:
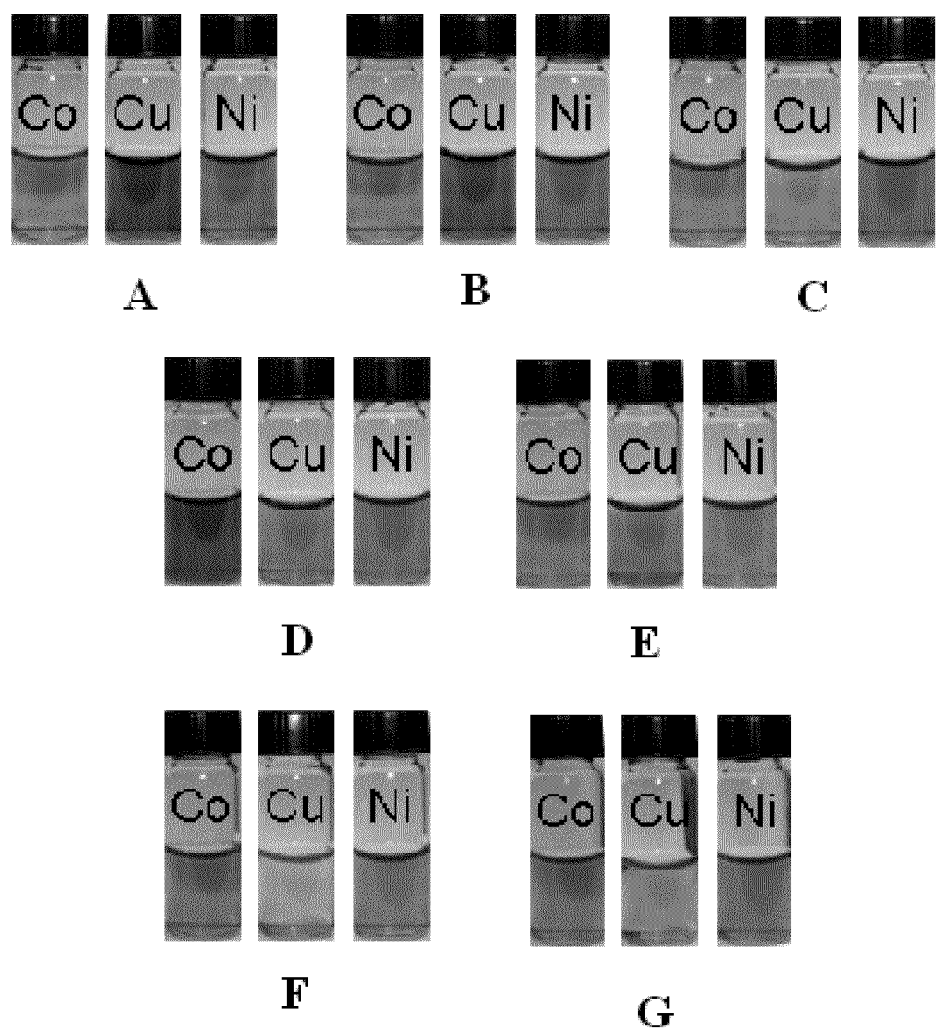
FIG. 6 is a photograph depicting the color patterns observed for various amines upon interaction with polymer 2 with different recognition elements. Sample A is 1,2-ethylenediamine, sample B is 1,3-propylenediamine, sample C is putrescine, sample D is cadaverine, sample E is histamine, sample F is spermidine, and sample G is spermine.

FIG. 6 is a photograph depicting the color changes observed for various amines in polymer 1 with different recognition elements. Sample A is ethylenediamine, sample B is propylenediamine, sample C is putrescine, sample D is cadaverine, sample E is histamine, sample F is spermidine, and sample F is spermine. The consumer or the inspector can use a color reference guide to aid in determining and differentiating the presence of various biogenic amines.
Lateral Flow Device One or more polymers or polymer compositions disclosed herein can be coated onto or into a solid or liquid component (e.g. a solid substrate) to form a device article. A polymer can adhere or be in communication with, for example, a substrate, through any appropriate means. If, for example, a substrate is used in a lateral flow device as described herein, it can be preferable that a polymer have some physical or chemical interaction with the substrate. For one contemplated lateral flow device, the extent of the interaction can change in the presence of different analyte species and can thereby produce a differential response to different analyte species.

In one aspect, a silica coated plate can be used as a substrate and a polymer can be introduced onto the substrate through any appropriate means (e.g., spotting the substrate with a capillary tube filled with polymer solution). In this example, if a stimulatory analyte (e.g., biogenic amine) is present in a sample (e.g. a water sample) that is developed with the silica substrate, the polymer can move laterally across the substrate. The distance that the polymer moves can be directly proportional to the amount (and type) of analyte present. The polymer can also become fluorescent under a stimulus (e.g., UV light) in the presence of an analyte. If the analyte is a diamine, for example, the polymer can change color from blue-purple to red-orange upon exposure to the diamine in the analyte solution. In addition the matrix can be nitrocellulose or mixtures of materials, for example, nitrocellulose and silica.

In one aspect, a lateral flow device as described herein can be a hand-held device. The device can be any appropriate size (e.g., for example, small enough to transport). One example is an assay device for determining the presence of one or more biogenic amines within an analyte, comprising a substrate having one or more detection zones wherein each zone contains a chromogenic responsive polymer that undergoes a chromogenic response upon reaction with a biogenic amine and wherein the response is dependent upon the biogenic amine present.

In a further aspect, an assay device for determining the presence of one or more biogenic amines within an analyte, comprising a substrate having a first end, a second end, and a plurality of channels wherein a different chromogenic responsive polymer is deposited onto each channel, the first end having a means for receiving an analyte and directing the analyte into each of the plurality of channels, wherein further each channel provides a chromogenic response that is specific to a particular biogenic amine.

FIG. 6 depicts a device that can be used by either the consumer or the inspector of food stuffs to determine the degree of spoilage. Such a device can function using a mechanism similar to that which ejects the ink stylus from an ink pen housing. A small needle can be ejected from the device that can be used to pierce a sample (liquid or solid). This piercing action can withdraw an amount of liquid from the sample via capillary action and wet a polymer-bound support, thereby initiating the development process. The distance which the polymer moves can be correlated to a particular type and/or amount of diamine present, or can be correlated to a particular type of diamine forming food product. FIG. 6 uses the example of analyzing for the level of a diamine or amine in a fish sample. The amount of amine present is correlated to the distance a sample will move on a substrate coated with one or more of the disclosed chromogenic responsive polymers.

While FIG. 6 displays one lane for a polymer, a plurality of lanes could be used, for example, to create a pattern. Alternatively, it can be possible for each lane to have specific sensitivity to a particular desired analyte. For example, if three lanes, lanes 1, 2, and 3, and three analytes, analyte 1, 2, and 3 were present, lane 1 could sense analyte 1, lane 2 could sense analyte 2, and lane 3 could sense analyte 3. For example, lane 1 could sense an analyte in tuna, lane 2 could sense an analyte in salmon, lane 3 could sense an analyte in beef, etc. As such, one embodiment of the device depicted in FIG. 6 relates to an assay device for determining the presence of one or more biogenic amines within an analyte, comprising a substrate having one or more detection zones wherein each zone contains a chromogenic responsive polymer that undergoes a chromogenic response upon reaction with a biogenic amine and wherein the response is dependent upon the biogenic amine present. Furthermore, the presence of this or these biogenic amines relates to the extent of spoilage of the food.

Dip-Stick Device

A device suitable for use with the disclosed compounds, compositions, and methods can be a dip-stick device. In one aspect, a dip-stick device can operate functionally similar to a pH dip-stick device. For example, different indicators (e.g., in the form of strips or pads) can be exposed to an analytical sample, and the result (e.g., a visible change) can be compared to a reference pattern (e.g., a pattern present on a device package).

Such a device can comprise a polymer or polymer composition, such as a polymer or polymer compositions disclosed herein. If a strip or pad is used in a device, a strip or pad can be impregnated with a sensing polymer. Such polymers can, for example, have different main-chain structures and/or different side-chain functionalities and/or different side-chain modifications of the same polymer, or the polymers can be in different matrices (e.g., polar and apolar polymer composites or immobilized solutions). These polymers can turn different colors in the presence of different types and amounts of analytes (e.g., a biogenic amine). A permeable, semi-permeable, or partially permeable membrane can be used that can allow sample into the device while at least partially keeping the polymer from leaching out of the device.

Figure 7:
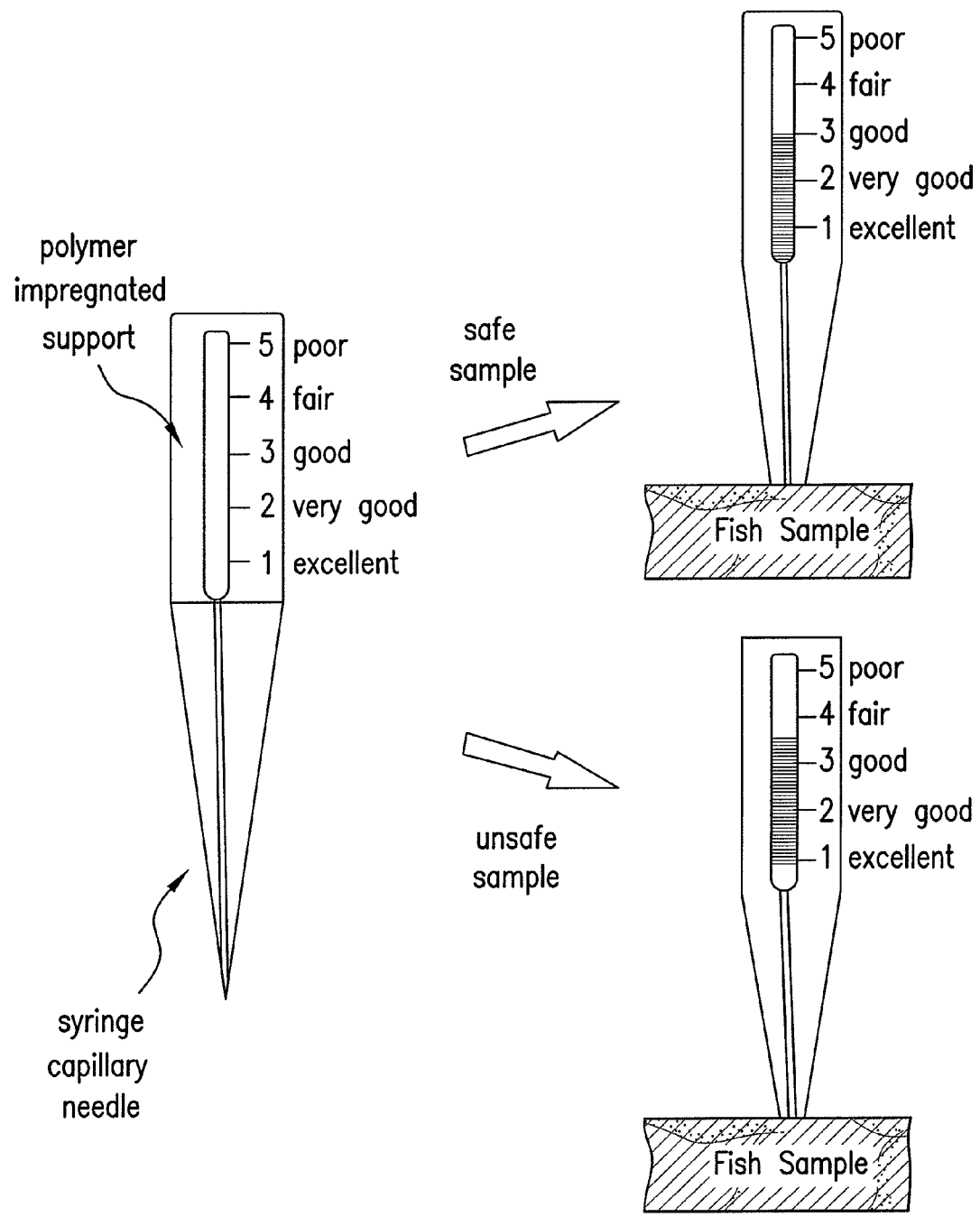
FIG. 7 depicts a device schematic that can be used by either the consumer or the inspector of food stuffs to determine the degree of spoilage.

FIG. 7, for example, displays an exemplary device composition that could be used with a dip-stick device. Zones A-C of the dip-stick in one embodiment can be correlated to the results depicted in FIG. 5. For example, zone A can comprise the polymer from Series No. 1, zone B the polymer from Series 2, and zone C the polymer from Series No. 3. An analyte applied to the dip-stick that registers the chromogenic response seen in the vials marked E would indicate the presence of putrescine. The identity of the amine in the analyte can be determined by comparing the color pattern along the vertical columns of vials depicted in FIG. 5.

Lateral Flow Assay Device

A lateral flow device suitable for use with the disclosed methods and compositions can be based on polymer aggregation. Such a device can be based on multiple interactions between an analyte and a receptor. For example, polymers in such a device can be used for aggregate formation thereby producing a yes or no (or 1 or 0) signal. Some polymers disclosed herein have multiple acidic side-chains and thereby can be suitable for detecting the presence of, for example, biogenic amines since most biogenic amines contain multiple basic amines. Alternatively, metal nano-particles or polymer microspheres coated with a polymer or polymer composition, such as a polymer or polymer compositions as disclosed herein, or coated, for example, with a carboxylic acid based compound or polymer could be used to produce a platform from which aggregation could stem.

Analytical Methods Using Chromogenic Responsive Polymers

The chromogenic responsive polymers can be used for analytical methods in determining the presence and concentration of one or more amines in an analyte. Using the measured absorbance of reference samples containing single amines and combinations of amines, the formulator can construct a reference library to determine the composition of amines in an analyte.

The following are put forth so as to provide those of ordinary skill in the art with a complete disclosure and description of how the compounds, compositions, articles, devices, and/or methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of conditions, e.g., component concentrations, desired solvents, solvent mixtures, temperatures, pressures and other reaction ranges and conditions that can be used to optimize the methods described herein. Only reasonable and routine experimentation will be required to optimize such process conditions.

Organic Solution Based Sensing Using Polymer 1

For analyses in organic media, absorbance studies were performed using a Beckman Coulter 640 DU spectrophotometer and quartz cuvets from Starna. $_1$H and $_{13}$C spectra were recorded on a Varian Mercury300 spectrometer operating at 300 and 75 MHz, respectively. MALDI-TOF MS was performed using a Bruker Ultraflex TOF/TQF mass spectrometer. 2, 2':5',2"-Terthiophene (Aldrich) was used as the matrix.

An exemplary, representative assay experiment used in combination with the methods disclosed herein. A polymer solution was prepared by adding 16 mg of 1 to N,N-dimethylformamide (1 mL) then sonicated for one hour. The resulting mixture was diluted with 1,4-dioxane (9 mL) and again sonicated for one hour. Subsequently, the mixture was filtered thru a 0.45 micron teflon disk to remove undissolved polymer. The orange filtrate (1 mL) was added to a mixture of acetonitrile (5 mL) and deionized water (250 μL). This preparation produces 6.25 mL of the purple working polymer solution. The 100 mM amine solutions (1,2-ethylenediamine, 1,3-propylenediamine, 1,4-butylenediamine, histamine, 1,5-pentylenediamine and 1,6-hexylenediamine) were prepared by adding 1,4-dioxane to the appropriate amount of amine. For each assay, the amine solution (50 μL) was added to polymer solution (1 mL) in a quartz cuvet and then shaken for 30 seconds before the absorbance was measured. Each amine was measured at five different concentrations: 1.5 and 3.5 mM, in triplicate and 0.5, 2.5, and 5.0 mM all with six replicates for a total of 24 measurements for each amine and 144 measurements overall. Spectral data was obtained from 300-750 nm for each experiment at 25° C.

In wet acetonitrile solution, the addition of each diamine to a solution of polymer 1 resulted in an immediate change in the solution color from purple to different shades of red. All spectral data were normalized such that the area under each absorption spectrum was equal to one. Analysis was performed on the response of the polymer across the entire spectrum using nine different wavelengths between 420 and 740 nm every 40 nm (Absorbance values above 420 nm were used to eliminate potential bias in the analysis due to absorption from histamine).

Figure 8:
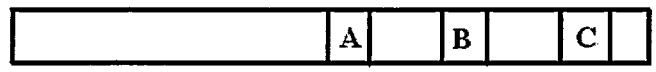
FIG. 8 depicts an exemplary dip-stick device, displaying multiple polymer composites that would generate a pattern for sensing biogenic amines.
Figure 9:
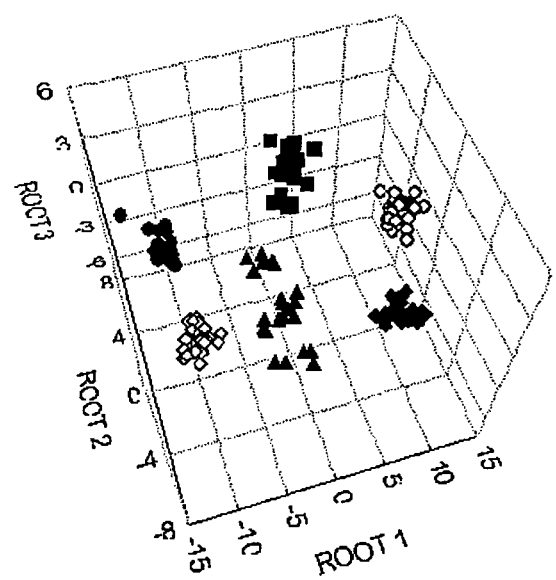
FIG. 9 depicts the projection of the LDA results in three dimensions for Polymer 1 differentiating structurally similar diamines. Each point in the plot contains information from the nine wavelengths taken from the spectrum for the specific diamine.

Absorbance data can be analyzed using pattern recognition protocols. Linear discriminant analysis (LDA), through commercially available software, was used to minimize variation within each diamine group while maximizing differences between each different diamine. FIG. 9 depicts the projection of the LDA results in three dimensions. Each point in the plot contains information from the nine wavelengths taken from the spectrum for the specific diamine. Using the leave-one-out cross-validation method, for this example, conjugated polymer 1 correctly classified 143 out of 144 measured samples (>99% accuracy). In addition, the polymer response can be dependant on the concentration of amine in solution. In the example depicted in FIG. 8, the absorbance maximum for the polymer-analyte complex did not follow a linear trend when correlated with amine concentration. The formulator can perform multiple linear regression on unnormalized absorbance data thereby predicting the expected value. Additional analysis using principal component analysis (PCA) can also further enhance the accuracy. Utilizing the disclosed methods, diamines can be detected and quantified in the nanomolar range (~100 nM).

Aqueous Based Sensing Using Polymer 2

For aqueous based sensing, absorbance studies were performed using a Beckman Coulter 640 DU spectrophotometer or a SPECTRAmax Plus plate reader from Molecular Devices in plastic (polypropylene) cuvets or plastic microtiter plates, respectively. All measurements were carried out in a Peltier thermostated sample holder maintained at 25° C. Canned tuna fish was purchased from area grocery stores.

The following example describes methods of sensing, identifying, and classifying structurally similar diamines using polymer 2 in the presence of a buffered aqueous media (i.e. a competitive solvent). The analysis carried out relied on the optical signature of a 1 mM aqueous solution of a polymer 2 responding to 1 eq. of amine in a solution of 40 mM HEPES buffer (pH 7.4) at a constant temperature.

For assay experiments carried out in water, deionized water can be used. HEPES buffer solution was prepared to the concentration of 50 mM as a stock solution and the pH was adjusted to 7.4 using a Thermo Orion pH reader. Solutions of the amines were prepared to the concentration of 10 mM in 50 mM HEPES buffer solution (pH=7.4). The polymer solution was prepared by adding 61.6 mg of 1 to 80 mL of deionized water and the pH was adjusted to 7.4 using 1 M NaOH and 1M HCl and then sonicated for thirty minutes. This preparation produces 80 mL of a 5 mM reddish/purple working polymer solution.

For spectroscopic assay analysis in water, the following is given as a representative procedure. A 5 mM stock solution of polymer 2 (pH=7.4) was loaded at 60 μl per well into a multi-well plate. To each well 30 μl of a 10 mM solution of amine was added. Finally 210 μl of 50 mM HEPES buffer solution (pH 7.4) was added for a total volume of 300 μl. Final concentrations in each well are: buffer=40 mM, polymer=1 mM, and amine=1 mM. The absorbance was measured from 300-700 nm with 47 replicates each. The entire spectrum between 350 and 700 nm every 10 nm (36 wavelengths) was used for the analysis. Absorbance values below 350 nm were excluded so that the assay would not be influenced by absorption from aromatic amines.

The formulator can reduce systematic errors and other sources of error by using techniques familiar to the artisan. Absorption spectra were recorded using a microtiter plate reader with the samples randomized on the plates to avoid systematic errors. For example, one method of reducing or minimizing systematic error, is to conduct replicate analyses. For example, 47 replicate analyses (282 total samples) were carried out on different days, using different solutions. The spectrum between 350-700 nm (at 10 nm intervals) was used for the analysis; 36 total wavelengths were analyzed, thereby providing a 36 dimensional data set. Absorbance values below about 350 nm were excluded in order to minimize the influence of aromatic analytes. The pH was controlled to ensure that discrimination between amines was based upon polymer response to the amine rather than pH changes.

Figure 10:
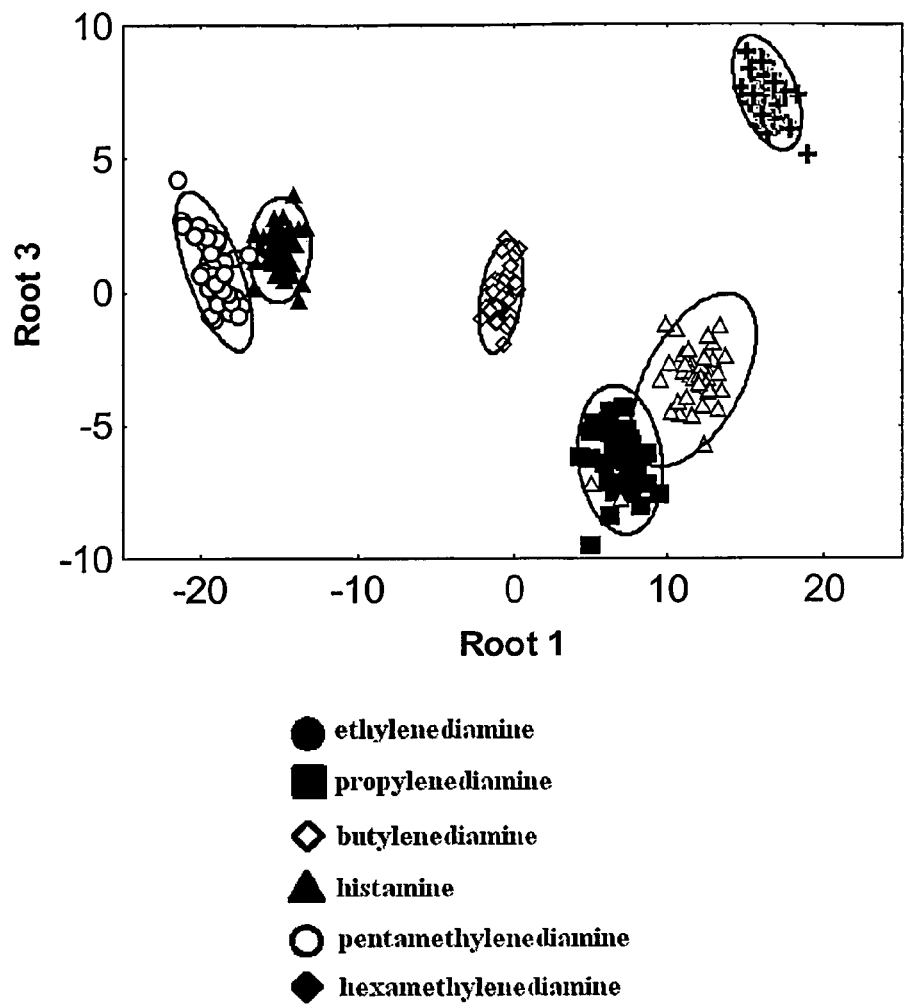
FIG. 10 depicts a plot of LDA results in two dimensions for detecting amines in highly competitive aqueous media using Polymer 2. Each axis of the LDA plot represents weighted combinations of the 36 dimensional data, where each point in the plot is an individual replicate that contains information from the 36 wavelengths of the relevant spectrum. The circles around each cluster represent 95% confidence limits.

FIG. 10 is a plot of LDA results in two dimensions for detecting amines in highly competitive aqueous media. Each axis of the LDA plot represents weighted combinations of the 36 dimensional data, where each point in the plot is an individual replicate that contains information from the 36 wavelengths of the relevant spectrum. The circles around each cluster represent 95% confidence limits. Leave-one-out cross-validation was used to estimate the predictive ability of the LDA model; this method showed excellent discrimination between amines with the analyte being accurately identifying the 99% of the time (i.e., 278/282 samples).

Aqueous Based Sensing Using Polymer 2 in a Fish Matrix

The following example is directed towards demonstrating the utility of the described design to detect differing amounts of biogenic amine in a food matrix, namely tuna fish extract. In this particular example, the exact nature of the biogenic amine present is histamine, the principle biogenic amine formed as tuna fish decomposes, i.e. spoils.

For fish assay analysis, the following is provided herein as a representative procedure. Generation of the "fish matrix" followed methods known in the art. Fresh canned tuna fish was drained and only solid meat was used. The meat (113.85 g) was blended with 10% (v/v) trichloroacetic acid (TCA, 200 mL) to extract biogenic amines. A 40 mL aliquot was centrifuged at 3000 rpm at 4° C. for 10 minutes to remove precipitated protein and other particulate. The liquid was decanted and washed with hexanes to remove lipids and other oils. The resulting aqueous solution was used as the fish matrix which was spiked with varying amounts of histamine. The 100 mM histamine stock solution was made by dissolving 184 mg histamine in 10 mL of 10% TCA. Twelve different concentrations of histamine in the fish matrix were generated from 0.0225 mM (2.5 ppm) to 4.5 mM (500 ppm). Each histamine spiked fish matrix was loaded at 20 µl per well into a multi-well plate (8 replicates). 280 µl of a 0.536 mM solution of polymer 2 in 50 mM HEPES (pH=7.4) was added to each well. The final polymer concentration was 0.5 mM. The entire spectrum between 350 and 700 nm every 10 nm (36 wavelengths) was used for the analysis.

Figure 3:
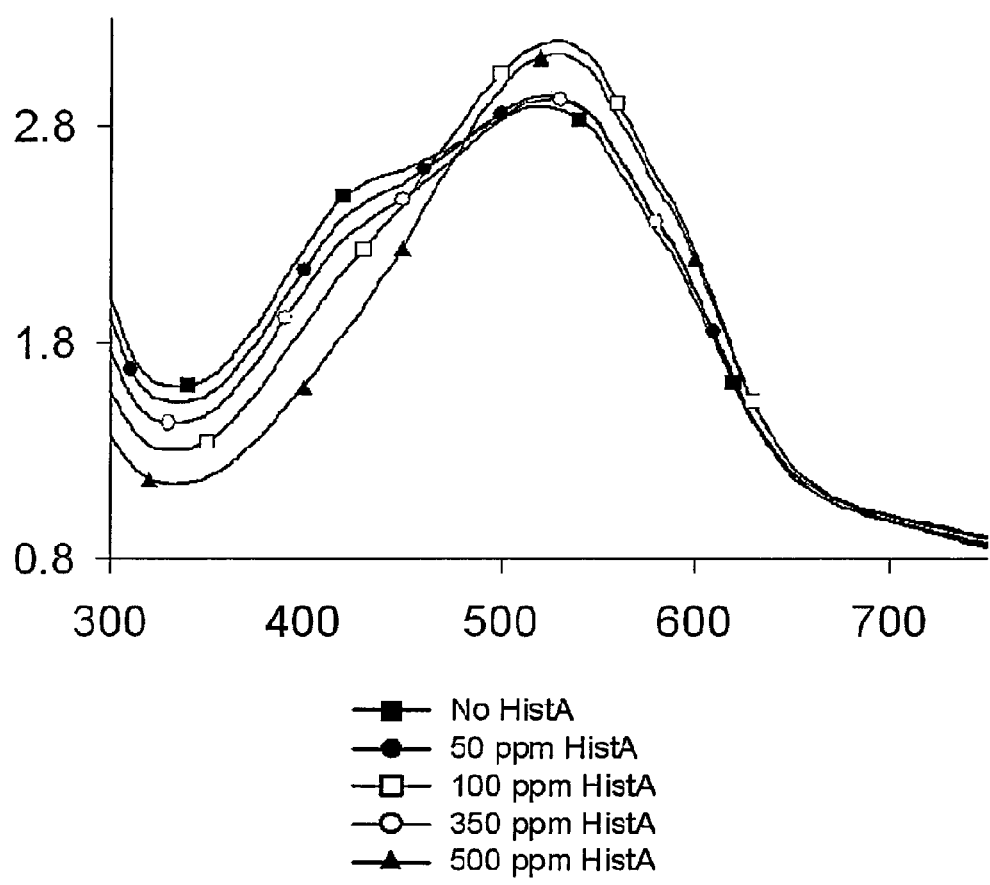
FIG. 3 depicts the change in the absorption spectrum of polymer 1 with increasing concentrations of histamine in a tuna fish matrix.
Figure 4:
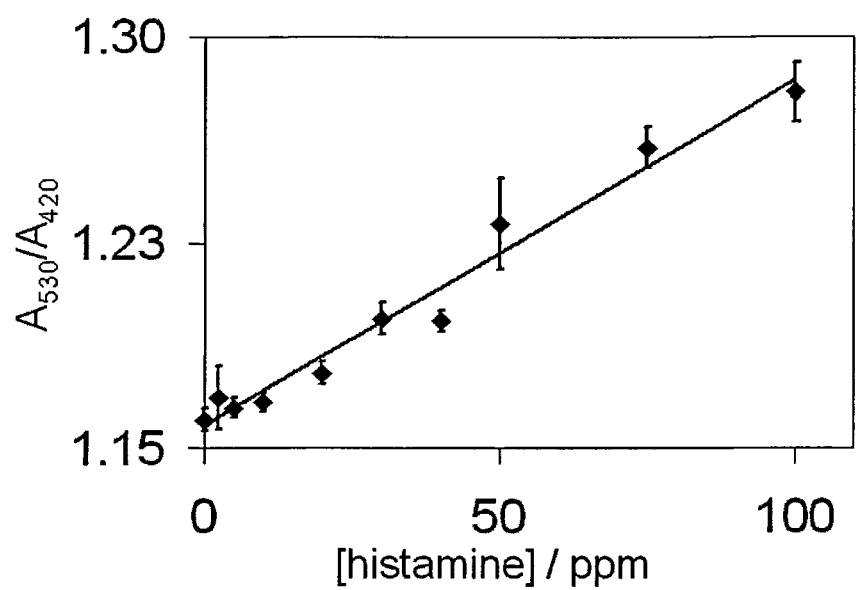
FIG. 4 depicts a linear ratiometric response ($A_{530}/A_{420}$) with increasing histamine concentration in a tuna fish matrix.

Polymer 2 was used to assess the amount of biogenic amine present in a fish sample. The most prevalent biogenic amine found in tuna is histamine. A tuna sample was obtained and spiked with histamine. The fish sample was processed by extracting the biogenic amines with trichloroacetic acid, while simultaneously precipitating undesired proteins. FIG. 3 depicts the change in the absorption spectrum of polymer 2 with increasing concentrations of histamine and therefore the sensitivity of the disclosed methods to indicate the degree of food spoilage. FIG. 4 depicts a linear ratiometric response ($A_{530}/A_{420}$) with increasing histamine concentration over the range useful for detecting food spoilage associated with food poisoning. The sensitivity of the described assay is better than the typical mammalian sense of smell. Specifically, this method could allow for the detection of the non-volatile biogenic amines at hazardous levels before the fish begins to smell bad (e.g., in the early stages of spoilage).

Aqueous Based Sensing Using Polymer 2 to Assess Fish Spoilage

The following example is directed toward the detection of biogenic amines in a sample of fish with the goal of determine the spoilage degree. In this particular example, the exact nature of the biogenic amines present was unknown. The general quality of the fish sample was measured as a function of the amount of biogenic amine present.

Specifically, the canned tuna used in this analysis was Bumblebee white albacore in water, purchased from a local supermarket. A solution of polymer 2 in aqueous sodium hydroxide (2.5 mM) was prepared by adding 1.1 mg of polymer 1 to 2.5 mL of deionized water followed by 0.05 mL of 2 N sodium hydroxide solution. The fish solutions were prepared by homogenizing canned tuna. About 5 grams of the fish was placed in unsealed vials and was set to spoil at 0, 4, 8, 24, and 48 hours. For each experiment, at the designated time, 10% (w/v) trichloroacetic acid (3 mL) was added to the fish flesh and minced using a mortar and pestle until a slush-like consistency was obtained. The fish slush was centrifuged at 3000 rpm (4° C.) for about 30 minutes. The fish extract (supernatant liquid) was removed with a pipette and allowed to equilibrate to 30° C. in a temperature bath. For each assay, 900 µL of the 50 mM HEPES solution (pH 7.4) was added to 50 µL of the polymer solution followed by 50 µL of the fish extract. The absorbance was obtained for each time for both polymer solutions.

Figure 11:
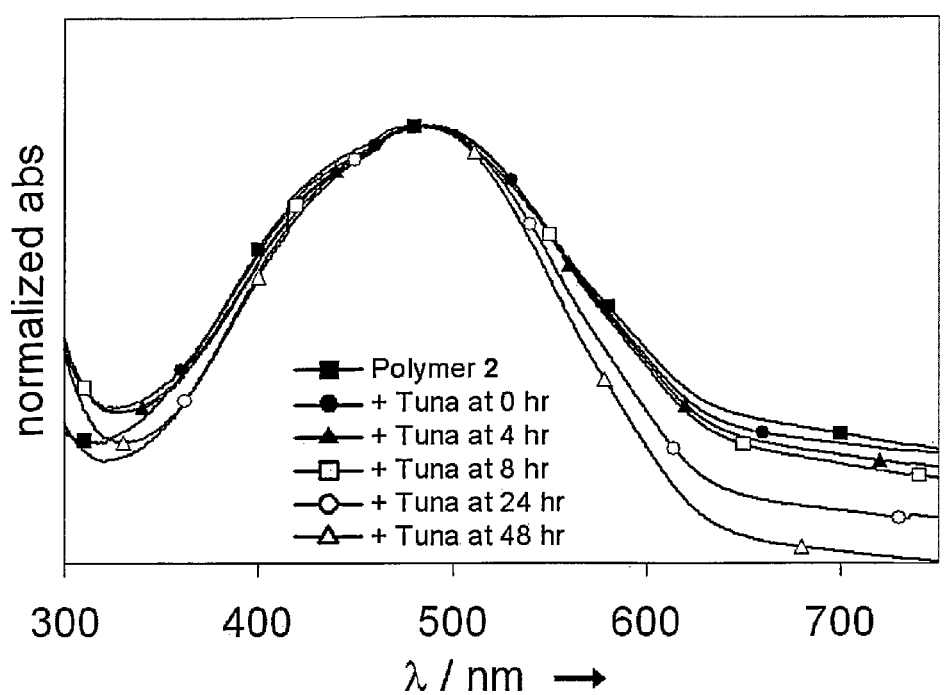
FIG. 11 shows the absorbance spectra of 2 responding to the addition of six different fish extracts from decaying tuna fish flesh over time.
Figure 12:
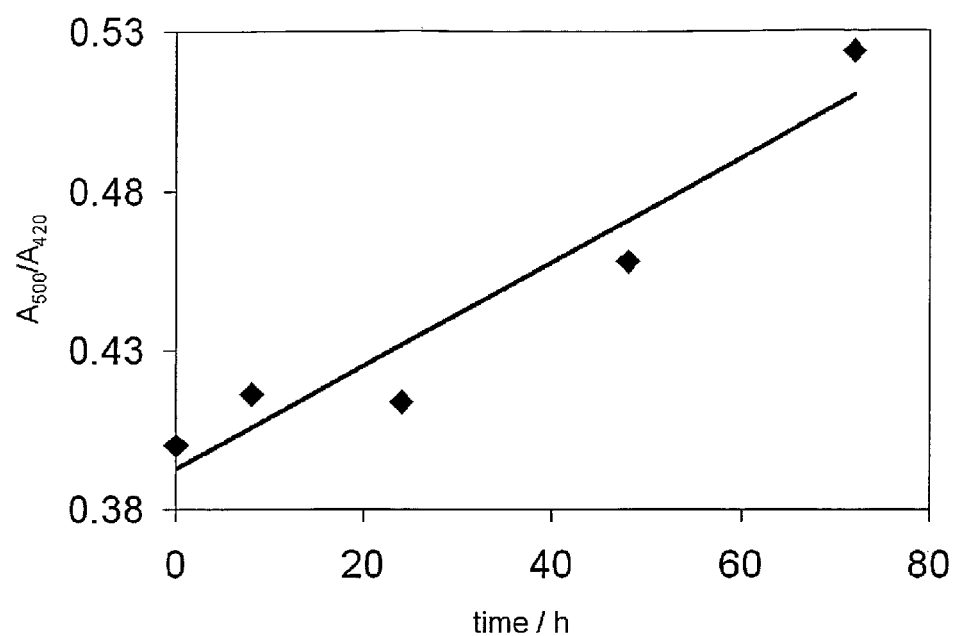
FIG. 12 depicts a linear ratiometric response ($A_{500}/A_{420}$) from Polymer 2 as tuna fish flesh decays over time.
Figure 13:
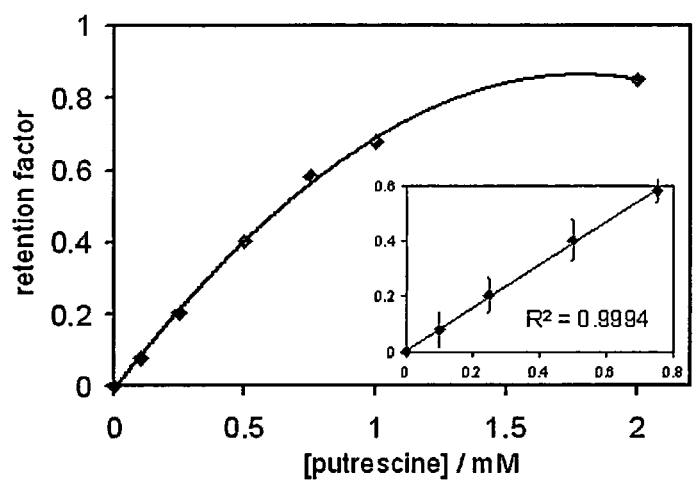
FIG. 13 depicts a plot of the polymer 2 response in the red channel from a lateral flow assay responding to putrescine at various concentrations.

FIG. 11 shows the absorbance spectra of 2 responding to the addition of six different fish extracts from decaying tuna fish flesh over time. With increasing concentration of biogenic amines in the fish extract, i.e. as the fish spoils over time, the polymer produces a unique chromogenic response. FIG. 12 shows the linear ratiometric response from this assay correlated to spoilage time.

Aqueous Based Sensing Using Polymer 2 Composites

The following example describes experiments directed at detecting biogenic amines with the polymer compositions of the present disclosure. In situ ion exchange was used to form polymer-metal composites based on 2+ cations. The polymer chosen to detect these amines was HT-poly(thiophene-3-propionate) (2), used in combination with three transition metal salts including Cobalt, Copper and Nickel.

A selected metal was first added to the polymer, and amines were subsequently detected and identified using the metallic polymer composition. HEPES buffer solution (50 mM) used in this Example was prepared using methods known in the art. The pH of the buffer solution was adjusted to 7.4. Amine solutions were prepared to concentrations of 100 mM (of amine) in the 50 mM HEPES buffer solution. A stock solution of 2 was prepared in HEPES buffer solution in a concentration of 5 mM polymer 2.

A 5 mM solution of the polymer 2 was loaded at 12 µl per well into a multi-well plate. Fifteen µl of a 100 mM solution of amine mixture was added to each well. Twelve µl of a 5 mM solution of transition metal salt was added to each well. The wells were then filled to a volume of 300 µl with 50 mM HEPES buffer solution, and the absorbance was subsequently measured. Twenty-eight replicates were completed for each mixture in each assay.

The addition of the transition metals to the polymer led to precipitation (FIG. 5, vial B). While not wishing to be bound by theory, it was believed that the subsequent addition of the amines competes with the polymer for metal binding and breaks up the aggregated polymer through coordination between the metal and the amine. This produces a "turn-on" sensor since the colorless solution becomes highly colored upon addition of amine, thereby enhancing the sensitivity and utility of the assay. A composite color signature or fingerprint of each polymer composite in the array responding differently to each analyte can be obtained from the chromic responses of the polymer array (FIG. 5, vials C-I). Advanced pattern recognition protocols are not required to differentiate the identity of the biogenic amine present. Rather, the unique color pattern produced clearly indicates the identity of the analyte by simple visual analysis (i.e. by eye).

Aqueous Based Sensing Using Polymer 2 Composites to Assess Biogenic Amine Mixtures These same polymer-metal composites described above can be used to analyze mixtures of biogenic amines. Three of the most common biogenic amines include putrescine, cadverine and histamine. Therefore, mixtures of these three targets were investigated based on the chromogenic response from the aggregate polymer-composites.

Figure 14:
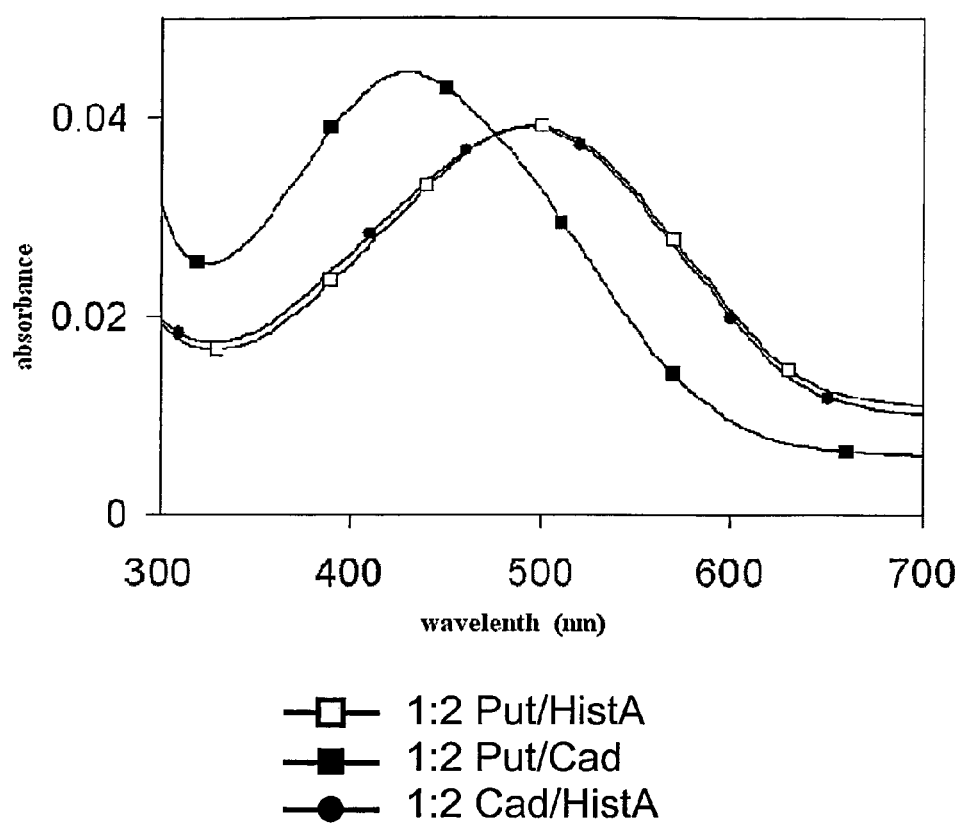
FIG. 14 depicts the absorbance spectra for combinations of amines. The line with clear squares represents a 1:2 mixture of putrescine and histamine, the line with solid squares represents a 1:2 mixture of putrescine and cadverine, and the line with solid circles represents a 1:2 mixture of cadaverine and histamine
Figure 15:
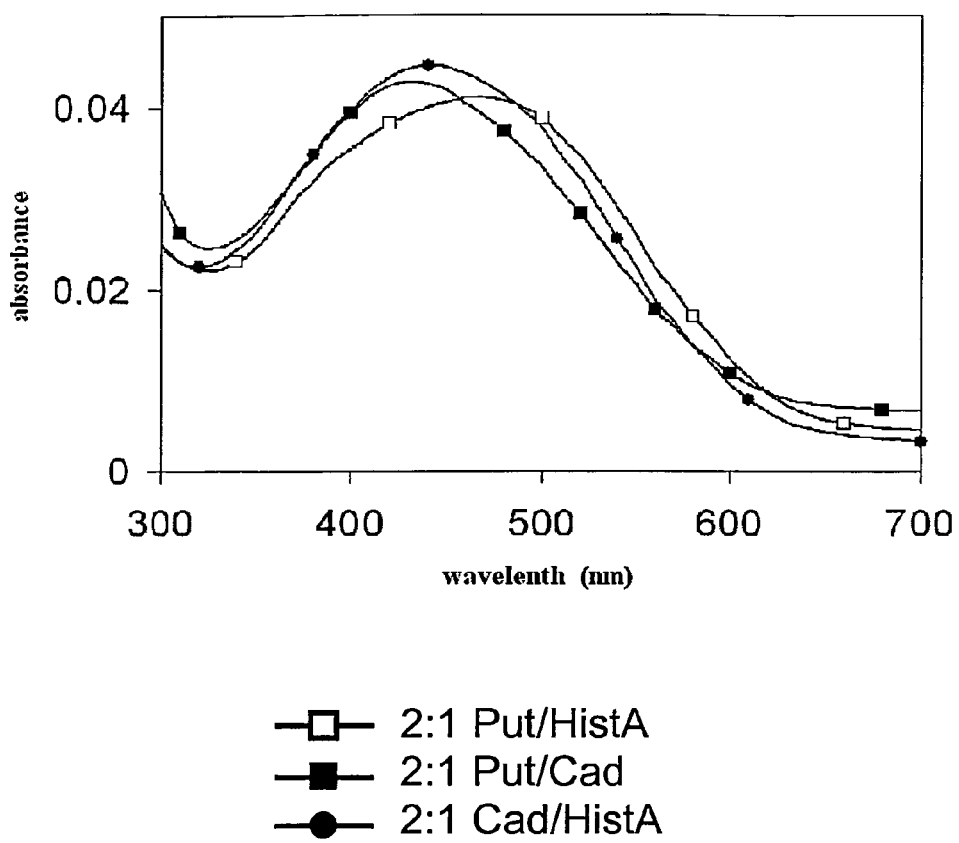
FIG. 15 depicts the absorbance spectra for combinations of amines. The line with clear squares represents a 2:1 mixture of putrescine and histamine, the line with solid squares represents a 2:1 mixture of putrescine and cadverine, and the line with circles represents a 2:1 mixture of cadaverine and histamine
Figure 16:
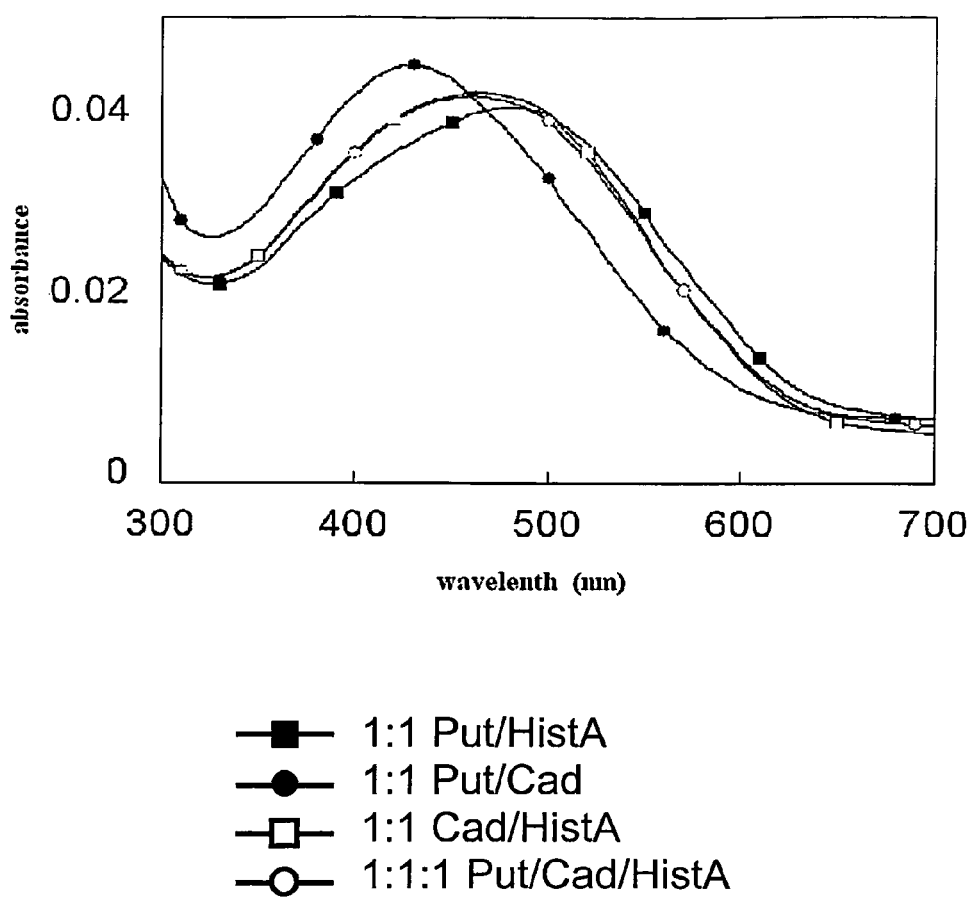
FIG. 16 depicts the absorbance spectra for combinations of amines. The line with the solid squares represents a 1:1 mixture of putrescine and histamine, the line with solid circles represents a 1:1 mixture of putrescine and cadverine, the line with clear squares represents a 1:1 mixture of cadaverine and histamine, and the line with clear circles represents a 1:1:1 mixture of putrescine, cadaverine and histamine.

The assay conditions were as described above. The amine mixtures were produced according to ratios that can be seen in the legend of FIGS. 14-16. The absorbance spectra for 0.4 mM of the polythiophene/metal composite sensor upon addition of 5 mM of the amine mixture were collected and normalized. FIGS. 14-16 depict the averaged absorbance spectra for polymer 2 on its own, and with $Co^{2+}$, $Cu^{2+}$ and $Ni^{2+}$ in response to combinations of three relevant biogenic amines: putrescine, caraverine and histamine. In FIG. 14, the line with clear squares represents a 1:2 mixture of putrescine and histamine, the line with solid squares represents a 1:2 mixture of putrescine and cadverine, and the line with solid circles represents a 1:2 mixture of cadaverine and histamine. In FIG. 15, the line with clear squares represents a 2:1 mixture of putrescine and histamine, the line with solid squares represents a 2:1 mixture of putrescine and cadverine, and the line with circles represents a 2:1 mixture of cadaverine and histamine. In FIG. 16, the line with the solid squares represents a 1:1 mixture of putrescine and histamine, the line with solid circles represents a 1:1 mixture of putrescine and cadverine, the line with clear squares represents a 1:1 mixture of cadaverine and histamine, and the line with clear circles represents a 1:1:1 mixture of putrescine, cadaverine and histamine.

LDA was performed on the spectral data to differentiate and classify the differences of the spectra from 420-700 nm (at 30 nm intervals) for each sensor element of the array. Twenty-eight replicates of each mixture were analyzed to ensure reproducibility of this approach. Table 1 lists the response of each sensor element of the array and the combined total response. Using the polymer/metal complex array, a 99% classification rate was obtained. The leave-one-out cross-validation number accuracy was found to be 97%. It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The differences in polymer responses provide a distinguishable optical signature for the analytes tested. These signatures can be further tuned to generate maximum responses that can be used to improve the detection of biogenic amines. Alternatively, these signals can be combined to provide an array based response, where the diagnostic value of the analysis can be enhanced when the response from multiple functional polymers or polymer composites are evaluated simultaneously. The optical signature can be used to determine relative concentrations of biogenic amines in foods by establishing trends between the spectra. The techniques used in these experiments can be used to detect the quality of other fish, meats, and other foods as a function of spoilage and bacterial contamination.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for detecting the presence of a biogenic amine, comprising:
   i) providing a chromogenic-responsive polymer comprising the structure:

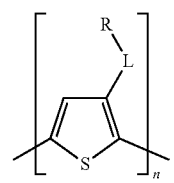

wherein R is —$CO_2M$;
   wherein L is —$CH_2$—; —$CH_2CH_2$—; —$CH_2CH_2CH_2$—; or —$CH_2CH_2CH_2CH_2$—; and
   wherein the index n has a value such that the polymer has a molecular weight of from about 1,000 Da to about 1,000,000 Da;
   and complexed with a plurality of substrate recognition elements, M, independently selected from a sodium ion, a cobalt ion, a copper ion, an iron ion, a nickel ion, a lanthanum ion, a europium ion, and a terbium ion;
   ii) contacting the polymer with an analyte comprising one or more amines; and
   iii) detecting a chromogenic response to the analyte by visual analysis of produced color as the amines coordinate the substrate recognition elements, M.

2. A method according to claim 1, wherein the polymer further comprises

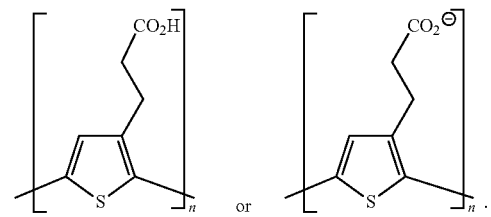

3. A method according to claim 2, wherein the polymer has the formula:

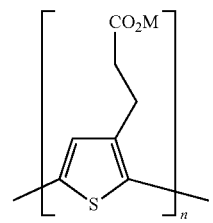

wherein M is chosen from $Na^+$, $Co^{2+}$, $Cu^{2+}$, and $Ni^{2+}$.

4. A method according to claim 1, wherein the analyte comprises one or more amines having the formula:

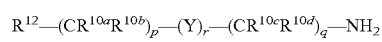

wherein $R^{10a}$, $R^{10b}$, $R^{10c}$, and $R^{10d}$ are each independently chosen from:
   i) hydrogen;
   ii) methyl; and
   iii) —$NH_2$;

the index p is an integer from 0 to 6;
the index q is an integer from 0 to 6;
Y is:
  i) —NH—; or
  ii) —(CR$^{11a}$R$^{11b}$)$_s$NH$_2$;
R$^{1a}$ and R$^{1b}$ are each independently:
  i) hydrogen; or
  ii) methyl;
the index r is 0 or 1;
the index s is an integer from 1 to 6; and
R$^{12}$ is chosen from:
  i) hydrogen;
  ii) —NH$_2$;
  iii) heterocyclic;
  iv) phenyl; or
  v) heteroaryl.

5. A method according to claim 1, wherein the analyte comprises one or more amines chosen from:

i) H$_2$N–CH$_2$CH$_2$–NH$_2$;
ii) H$_2$N–(CH$_2$)$_3$–NH$_2$;
iii) H$_2$N–(CH$_2$)$_4$–NH$_2$;
iv) H$_2$N–(CH$_2$)$_5$–NH$_2$;
v) H$_2$N–(CH$_2$)$_6$–NH$_2$;
vi) H$_2$N–(CH$_2$)$_3$–NH–(CH$_2$)$_4$–NH$_2$;
vii) H$_2$N–CH$_2$CH$_2$–NH–CH$_2$CH$_2$–NH–CH$_2$CH$_2$–NH$_2$;
viii) H$_2$N–(CH$_2$)$_3$–NH–(CH$_2$)$_4$–NH–(CH$_2$)$_3$–NH$_2$; and
ix) histamine (4-(2-aminoethyl)-1H-imidazole).

6. A method according to claim 1, wherein the analyte further comprises a solvent.

7. A method according to claim 6, wherein the solvent is water.

8. A method according to claim 6, wherein the solvent is chosen from a C$_1$-C$_{10}$ alcohol, a C$_3$-C$_6$ ester, a C$_3$-C$_6$ ketone, a C$_4$-C$_8$ ether, a C$_{1-5}$ nitrile, a C$_1$-C$_4$ di-alkylformamide, a C$_1$-C$_4$ di-alkylsulfoxide, and mixtures thereof.

9. A method according to claim 1, wherein the analyte further comprises a solvent chosen from water, acetonitrile, dimethylformamide, dimethylsulfoxide, methyl ethyl ketone, methyl acetate, ethyl acetate, and methyl tert-butyl ether.

10. A method according to claim 1, wherein the analyte further comprises a buffer.

11. A method according to claim 1, wherein the pH of the analyte is from about 6 to about 8.

12. A method according to claim 1, wherein the chromogenic response is visible light absorption or emission.

13. A method according to claim 1, wherein the analyte is taken from a food source.

14. A method according to claim 1, wherein each M is chosen from Na$^+$, Co$^{2+}$, Cu$^{2+}$, and Ni$^{2+}$.

15. A method according to claim 1, wherein each M is chosen from an alkali metal, an alkali earth metal, a transition metal, and a lanthanide metal.

16. A method according to claim 1, wherein each M is chosen from La$^{3+}$, Eu$^{3+}$ and Tb$^{3+}$.

17. A method according to claim 1, wherein each M is chosen from Co$^{2+}$, Cu$^{2+}$, Fe$^{2+}$, Ni$^{2+}$.

18. A method for detecting the presence of a biogenic amine, comprising:
  i) providing a chromogenic-responsive polymer comprising the structure:

[thiophene polymer with R,L substituent, repeat unit n]

wherein R is —CO$_2$M;
  wherein L is —CH$_2$—; —CH$_2$CH$_2$—; —CH$_2$CH$_2$CH$_2$—; or —CH$_2$CH$_2$CH$_2$CH$_2$—; and
  wherein the index n has a value such that the polymer has a molecular weight of from about 1,000 Da to about 1,000,000 Da;
  and complexed with a plurality of substrate recognition elements, M, independently selected from a nickel ion, a cobalt ion, and a copper ion;
  ii) contacting the polymer with an analyte comprising one or more amines; and
  iii) detecting a chromogenic response to the analyte by visual analysis of produced color as the amines coordinate the substrate recognition elements, M.

19. The method according to claim 18, wherein the polymer has the formula:

[thiophene polymer with CO$_2$M-CH$_2$CH$_2$- substituent, repeat unit n]

20. The method according to claim 18, wherein one or more of M is Co$^{2+}$, Cu$^{2+}$, or Ni$^{2+}$.

* * * * *